(12) United States Patent
Harrich

(10) Patent No.: US 8,828,933 B2
(45) Date of Patent: Sep. 9, 2014

(54) MUTANT TAT PROTEINS AND USES THEREOF

(75) Inventor: David Harrich, Strafford Heights (AU)

(73) Assignee: The Council of the Queensland Institute of Medical Research, Queensland (AU)

(*) Notice: Subject to any disclaimer, the term of this patent is extended or adjusted under 35 U.S.C. 154(b) by 55 days.

(21) Appl. No.: 13/292,425

(22) Filed: Nov. 9, 2011

(65) Prior Publication Data

US 2012/0115775 A1    May 10, 2012

Related U.S. Application Data

(60) Provisional application No. 61/411,977, filed on Nov. 10, 2010.

(51) Int. Cl.
| | | |
|---|---|---|
| *A61K 38/16* | (2006.01) | |
| *C12N 15/49* | (2006.01) | |
| *C12N 15/63* | (2006.01) | |
| *C12N 1/21* | (2006.01) | |
| *A61P 31/18* | (2006.01) | |
| *C12N 5/10* | (2006.01) | |
| *C12N 1/19* | (2006.01) | |
| *C07K 14/155* | (2006.01) | |
| *C12P 21/02* | (2006.01) | |

(52) U.S. Cl.
USPC ...... 514/3.8; 530/350; 536/23.72; 435/320.1; 435/69.1; 435/367; 435/369; 435/325

(58) Field of Classification Search
USPC ............................................................ 514/3.8
See application file for complete search history.

(56) References Cited

FOREIGN PATENT DOCUMENTS

WO    WO 03/054006 A2 *   7/2003

OTHER PUBLICATIONS

Ulich et al. (Inhibition of human immunodeficiency virus type 1 replication is enhanced by a combination of transdominant Tat and Rev proteins., J. Virol (1996), vol. 70 (7), p. 4871).*
Jeang (HIV-1 Tat: Structure and Function, Mar. 7, 1997).*
Meredith et al. (Potent Inhibition of HIV-1 Replication by a Tat Mutant., Plos One, vol. 4 (11), published online—Nov. 10, 2009).*
Ulich et al., Inhibition of human immunodeficiency virus type 1 replication is enhanced by a combination of transdominant Tat and Rev proteins. J Virol 70: 4871-4876 (1996).
Vivès et al., A truncated HIV-1 Tat protein basic domain rapidly translocates through the plasma membrane . . . J Biol Chem 272: 16010-16017 (1997).
Apolloni et al., Human immunodeficiency virus type 1 protease regulation of tat activity is essential for efficient . . . J Virol 77: 9912-9921 (2003).
Apolloni et al., The HIV-1 Tat protein stimulates reverse transcription in vitro. Curr HIV Res 5: 473-483 (2007).
Arrigo et al., Characterization and expression of novel singly spliced RNA species of human immunodeficiency virus type 1. J Virol 64: 4585-4588 (1990).
Barillari et al., The Tat protein of human immunodeficiency virus type 1 . . . Proc Natl Acad Sci USA 90: 7941-7945 (1993).
Berkhout et al.,) Tat trans-activates the human immunodeficiency virus through a nascent RNA target. Cell 59: 273-282 (1989.
Cardarelli et al., In vivo study of HIV-1 Tat arginine-rich motif unveils its transport properties. Mol Ther 15: 1313-1322 (2007).
Echetebu et al., Construction and characterization of a potent HIV-2 Tat transdominant mutant protein. J Acquir Immune Defic Syndr 7: 655-664 (1994).
Efthymiadis et al., The HIV-1 Tat nuclear localization sequence confers novel nuclear import properties. J Biol Chem 273: 1623-1628 (1998).
Hauber et al., Mutational analysis of the conserved basic domain of human immunodeficiency virus tat protein. J Virol 63: 1181-1187 (1989).
Hauber et al., Trans-activation of human immunodeficiency virus gene expression is mediated by . . . Proc Natl Acad Sci USA 84: 6364-6368 (1987).
Hope et al., Mutational analysis of the human immunodeficiency virus type 1 Rev transactivator: essential residues . . . J Virol 64: 5360-5366 (1990).
Houzet et al., Nucleocapsid mutations turn HIV-1 into a DNA-containing virus. Nucleic Acids Res 36: 2311-2319 (2008).
Jeang et al., Multifaceted activities of the HIV-1 transactivator of transcription, Tat. J Biol Chem 274: 28837-28840 (1999).
Li, Protein B23 is an important human factor for the nucleolar localization of the human immunodeficiency virus protein Tat. J Virol 71: 4098-4102 (1997).
Malim et al., Mutational definition of the human immunodeficiency virus type 1 Rev activation domain. J Virol 65: 4248-4254 (1991).
Orsini et al., Inhibition of human immunodeficiency virus type 1 and type 2 Tat function by transdominant Tat protein localized . . . J Virol 70: 8055-8063 (1996).
Pearson et al., A transdominant tat mutant that inhibits tat-induced gene expression from the human immunodeficiency virus . . . Proc Natl Acad Sci USA 87: 5079-5083 (1990).
Rossi et al., Inhibition of HIV-1 replication by a Tat transdominant negative mutant in human peripheral blood . . . Gene Ther 4: 1261-1269 (1997).
Ruben et al., Structural and functional characterization of human immunodeficiency virus tat protein. J Virol 63: 1-8 (1989).
Truant et al., the arginine-rich domains present in human immunodeficiency virus type 1 Tat and Rev function . . . Mol Cell Biol 19: 1210-1217 (1999).

* cited by examiner

*Primary Examiner* — James H Alstrum Acevedo
*Assistant Examiner* — Tara Martinez
(74) *Attorney, Agent, or Firm* — Womble Carlyle Sandridge & Rice LLP

(57) ABSTRACT

Disclosed are viral proteins associated with Human Immunodeficiency Virus (HIV) infections and mutants thereof, particularly, mutant Tat proteins capable of modulating multiple steps of the HIV-1 replication cycle. Also provided are methods of using the mutant Tat proteins, and pharmaceutical compositions comprising the same, for prevention and treatment of HIV-1 infections, and/or symptoms associated therewith.

6 Claims, 11 Drawing Sheets

A

B

C

MUTANT TAT PROTEINS AND USES THEREOF

CROSS REFERENCE TO RELATED APPLICATION

This application claims priority to and benefit of U.S. Provisional Application No. 61/411,977, filed Nov. 10, 2010, which is herein incorporated by reference in its entirety.

FIELD OF THE INVENTION

THIS INVENTION relates to viral proteins associated with Human Immunodeficiency Virus (HIV) infections and mutants thereof. More particularly, this invention relates to mutant Tat proteins capable of modulating multiple steps of the HIV-1 replication cycle. The invention also relates to methods of using the mutant Tat proteins, and pharmaceutical compositions comprising the same, for prevention and treatment of HIV-1 infections, and/or symptoms associated therewith.

BACKGROUND OF THE INVENTION

Tat is an essential HIV-1 regulatory protein whose best described role is to promote high levels of viral gene expression via interactions with the HIV-1 transactivation response element (TAR) RNA (Dayton et al., 1986; Hauber et al., 1987). Full-length Tat is encoded by two exons comprising 101 amino acids (varying between 99 and 104 residues) and represents the most abundant form of Tat from patient derived HIV-1. The first exon is organized into two major domains: the activation domain, which interacts with numerous cellular proteins including cyclin T1, and the basic domain, which is primarily comprised of arginine and lysine residues. The basic domain (amino acids 49-57) is required for many of Tat's activities including nuclear localization (Hauber et al., 1989; Ruben et al., 1989) and TAR binding (Berkhout et al., 1989). The basic domain has also been reported to facilitate other Tat activities such as membrane transduction (Vivès et al., 1997), assisting HIV-1 reverse transcription (Apolloni et al., 2003) and augmenting integrin receptor binding (Barillari et al., 1993). A transdominant negative mutant is typically an altered form of a protein that can inhibit the normal function of its wild type counterpart. Engineered Tat proteins with altered basic domains possess transdominant negative phenotypes against wild type Tat. However, previous studies of Tat transdominance have used one-exon tat mutants encoding truncated proteins of 72 amino acids or less. For example, Tat truncated at residue 53 can suppress transactivation initiated by wild type Tat (Pearson et al., 1990). This is despite the mutant localizing mainly to the cytoplasm of the cell, in contrast to wild type Tat, which localizes to the nucleus. One exon tat mutants with a deleted basic domain or where the basic domain has been substituted with neutrally-charged amino acids also recapitulate the transdominant negative effects on transactivation (Orsini & Debouck, 1996; Ulich et al., 1996). Localization of Tat mutants to the nucleus, via fusion of the Tat nuclear localization signal to their carboxy termini, results in retention of the transdominant negative phenotype (Orsini & Debouck, 1996). Moreover, mutations in the activation domain of the Tat mutant, which normally suppress the transactivation function of wild type Tat, can suppress transdominance (Orsini & Debouck, 1996). The mechanism of transdominance of Tat basic-domain mutants is unclear.

SUMMARY OF THE INVENTION

The present invention has arisen after the inventor surprisingly, discovered that a mutant Tat protein comprising a modified basic domain, and an amino acid sequence encoded by exon 2 of the Tat gene, is capable of at least partly inhibiting multiple steps in the HIV-1 replication cycle. Unexpectedly, the isolated mutant Tat protein suppressed both Tat-mediated transactivation and Rev-mediated transport of HIV-1 mRNA. Furthermore, virions produced by cells expressing the mutant Tat protein were found to have reduced infectivity, due to a decreased ability to undergo reverse transcription.

In a first aspect, the invention therefore provides an isolated mutant Tat protein comprising (i) an amino acid sequence of (a) an activation domain, and (b) an amino acid sequence of a modified basic domain; and (ii) another amino acid sequence that is encoded by a nucleotide sequence of exon 2 of a Tat gene.

In one embodiment, the amino acid sequence in (ii) comprises a glycine at a position corresponding to residue 79 of the amino acid sequence encoded by exon 2 of the Tat gene. Preferably, the amino acid sequence in (ii) comprises an RGD amino acid sequence, wherein the glycine is at a position corresponding to residue 79 of the amino acid sequence encoded by exon 2 of the Tat gene.

In a second aspect, the invention comprises a method of producing an isolated mutant Tat protein comprising (i) an amino acid sequence of (a) an activation domain, and (b) an amino acid sequence of a modified basic domain; and (ii) another amino acid sequence that is encoded by a nucleotide sequence of exon 2 of a Tat gene, said method comprising the step of introducing one or more amino acid modifications into said basic domain, to thereby produce said isolated mutant Tat protein.

In one embodiment, the amino acid sequence in (ii) comprises a glycine at a position corresponding to residue 79 of the amino acid sequence encoded by exon 2 of the Tat gene. Preferably, the amino acid sequence in (ii) comprises an RGD amino acid sequence, wherein the glycine is at a position corresponding to residue 79 of the amino acid sequence encoded by exon 2 of the Tat gene.

Preferably, said isolated mutant Tat protein is capable of modulating one or more steps of the HIV-1 replication cycle. Suitably, said isolated mutant Tat protein at least partly inhibits, suppresses, prevents, or otherwise hinders, one or more biological activities selected from the group consisting of Tat transactivation, Rev-dependent viral mRNA transport, and reverse transcription.

Suitably, said modified basic domain comprises one or more amino acid modifications. Preferably, said one or more acid modifications are amino acid substitutions, wherein one or more amino acids of the basic domain are substituted for, replaced by, or otherwise changed to, one or more non-basic amino acids. Suitably, said one or more non-basic amino acids are neutral amino acids. Said one or more neutral amino acids may be glycine and/or alanine amino acids.

In one particularly preferred embodiment, the basic domain of the isolated mutant Tat protein comprises an amino acid sequence as set forth in FIG. 1 (i.e., residues 49-57 of SEQ ID NO:1).

The invention according to the first and second aspects includes fragments, variants and derivatives of the isolated mutant Tat proteins of the invention.

In a third aspect, the invention provides an isolated nucleic acid encoding an isolated mutant Tat protein according to the first aspect, or an isolated mutant Tat protein produced according to the method of the second aspect.

The invention according to the third aspect includes fragments, variants and derivatives of the isolated nucleic acids of the invention.

In a fourth aspect, the invention provides a genetic construct comprising an isolated nucleic acid according to the third aspect, operably linked to one or more additional nucleotide sequences.

Preferably, said genetic construct is an expression construct. Suitably, said expression construct is a retroviral construct. In one particular embodiment, said retroviral construct is a lentiviral vector. In another particular embodiment, said retroviral construct is a non-lentiviral vector. Said non-lentiviral vector may be a Murine leukaemia virus (MLV)-based retroviral vector.

In a fifth aspect, the invention provides a host cell comprising a genetic construct according to the fourth aspect.

In a sixth aspect, the invention provides a method of producing an isolated mutant Tat protein according to the first aspect in recombinant form, said method including the steps of: (i) culturing a host cell containing an expression construct according to the fourth aspect such that said mutant Tat protein is expressed in said host cell; and (ii) isolating said mutant Tat protein.

In a seventh aspect, the invention provides an antibody, or antibody fragment, which specifically binds, and/or is raised against, (i) an isolated mutant Tat protein according to the first aspect; and/or (ii) an isolated mutant Tat protein produced according to the method of the second aspect.

In an eighth aspect, the invention provides an pharmaceutical composition comprising (i) an isolated mutant Tat protein according to the first aspect; (ii) an isolated mutant Tat protein produced according to the second aspect; (iii) an isolated nucleic acid according to the third aspect; (iv) a genetic construct according to the fourth aspect; and/or (v) a host cell according to the fifth aspect, and a carrier, diluent or excipient.

In a ninth aspect, the invention provides a method of treating or preventing, an HIV infection in a host, said method including the step of administering (i) an isolated mutant Tat protein according to the first aspect; (ii) an isolated mutant Tat protein produced according to the method of the second aspect; (iii) a nucleic acid according to the third aspect; (iv) a genetic construct according to the fourth aspect; (v) a host cell according to the fifth aspect; and/or (vi) a pharmaceutical composition according to the eighth aspect, to said host, to thereby treat or prevent said HIV infection, and/or one or more symptoms associated therewith, in said host, or in one or more cells or tissues of said host.

Preferably, said HIV infection is an HIV-1 infection.

In an tenth aspect, the invention provides a method of inhibiting, suppressing, or hindering Tat-mediated transactivation in a host, said method including the step of administering (i) an isolated mutant Tat protein according to the first aspect; (ii) an isolated mutant Tat protein produced according to the method of the second aspect; (iii) a nucleic acid according to the third aspect; (iv) a genetic construct according to the fourth aspect; (v) a host cell according to the fifth aspect; and/or (vi) a pharmaceutical composition according to the eighth aspect, to thereby inhibit, suppress, or hinder said Tat-mediated transactivation in said host, or in one or more cells or tissues of said host.

In an eleventh aspect, the invention provides a method of inhibiting, suppressing, or reducing Rev-mediated transport of HIV-1 mRNA in a host, said method including the step of administering (i) an isolated mutant Tat protein according to the first aspect; (ii) an isolated mutant Tat protein produced according to the method of the second aspect; (iii) a nucleic acid according to the third aspect; (iv) a genetic construct according to the fourth aspect; (v) a host cell according to the fifth aspect; and/or (vi) a pharmaceutical composition according to the eighth aspect, to thereby inhibit, suppress or reduce said Rev-mediated transport of HIV-1 mRNA in said host, or in one or more cells or tissues of said host.

In a twelfth aspect, the invention provides a method of inhibiting suppressing or decreasing HIV-1 virion reverse transcription and/or infectivity in a host, said method including the step of administering (i) an isolated mutant Tat protein according to the first aspect; (ii) an isolated mutant Tat protein produced according to the method of the second aspect; (iii) a nucleic acid according to the third aspect (iv) a genetic construct according to the fourth aspect; (v) a host cell according to the fifth aspect; and/or (vi) a pharmaceutical composition according to the eighth aspect, to thereby inhibit, suppress or decrease HIV-1 virion reverse transcription and/or infectivity in said host, or in one or more cells or tissues of said host.

The methods of the ninth, tenth, eleventh, and twelfth aspects may include a step that comprises adoptive cell therapy, such as adoptive T-cell therapy.

The host may be any animal, inclusive of mammals such as domestic animals, livestock, performance animals and humans. Preferably, the host is a human.

Throughout this specification, unless otherwise indicated, "comprise", "comprises" and "comprising" are used inclusively rather than exclusively, so that a stated integer or group of integers may include one or more other non-stated integers or groups of integers.

The MAGI (black circles), MAGI/EGFP (black diamonds) and MAGI/Nullbasic-EGFP (white diamonds) cell lines were infected with equal amounts of pGCH-derived virions (500 ng CA-equivalent per 106 cells) before viral replication was monitored over a 14-day period. Log values of virion CA levels measured in the culture supernatants are shown plotted against time. Obelisks ({) indicate observations of syncytia and cell death in the MAGI and MAGI/EGFP cell lines at 9 days post-infection. Data points represent the means and standard deviations of triplicate assays in two independent experiments.

Figure 9:
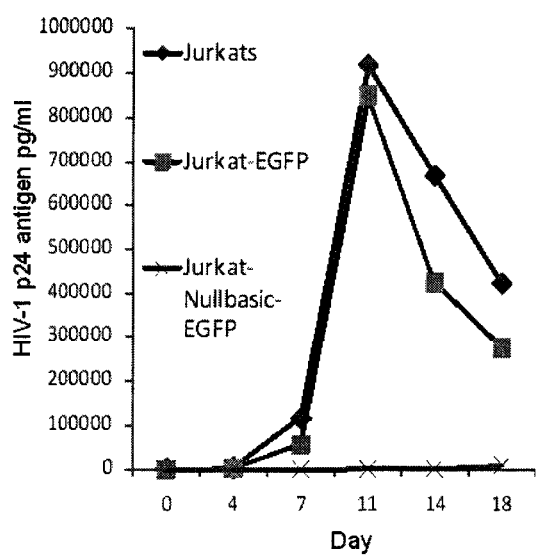

FIG. 9. Nullbasic-EGFP blocks HIV-1 infection in Jurkat cells. Jurkat T cells were transduced with MoMLV vectors conveying either Nullbasic-EGFP or EGFP. The transduced cells were FACS sorted and EGFP positive cells were kept. Jurkat-Nullbasic-EGFP, Jurkat-EGFP or parental Jurkat cells were infected with HIV-1 (1000 $TCID_{50}$). The cells were grown for three weeks and samples of the culture supernatant were collected every three or four days. The samples were tested for HIV-1 CAp24 by ELISA as indicated. While HIV-1 was able to grow in Jurkat-EGFP and Jurkat cells, HIV-1 did not replicate in Jurkat-Nullbasic-EGFP cells indicating that Nullbasic was able to protect the cells from HIV infection. The experiment was repeated eight times with identical results.

Figure 10:
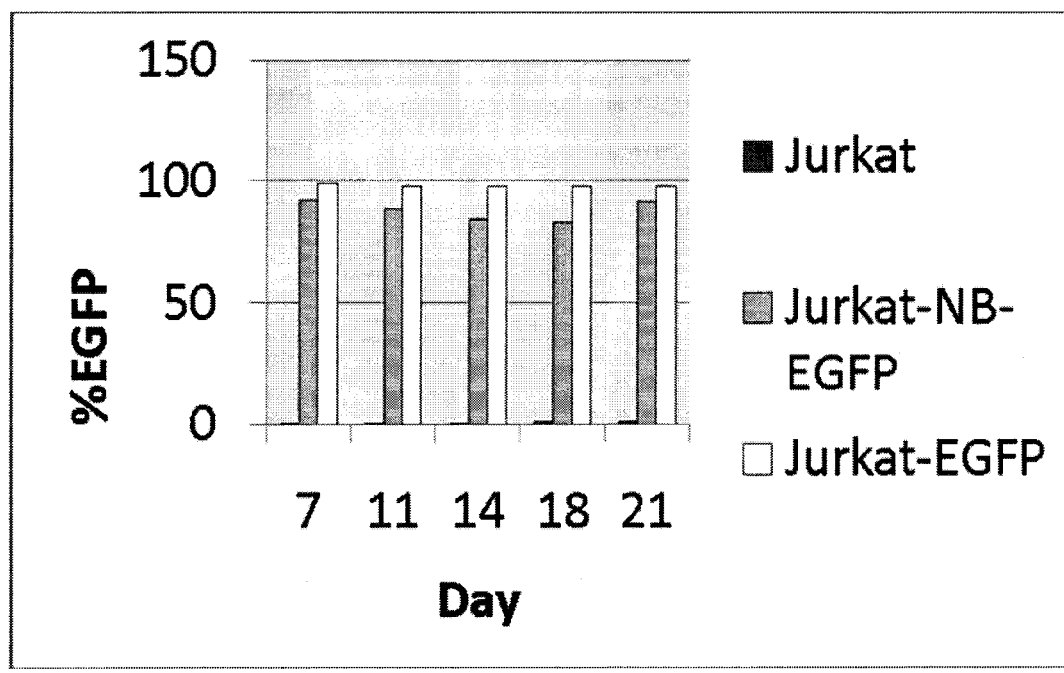

FIG. 10. Nullbasic was stably maintained by transduced Jurkat cells. Transduced Jurkat cells were assayed by flow cytometry to determine if Nullbasic was expressed during an HIV-1 infection. As shown, all cells retained high levels of EGFP indicating that Nullbasic was stably maintained.

Figure 11:
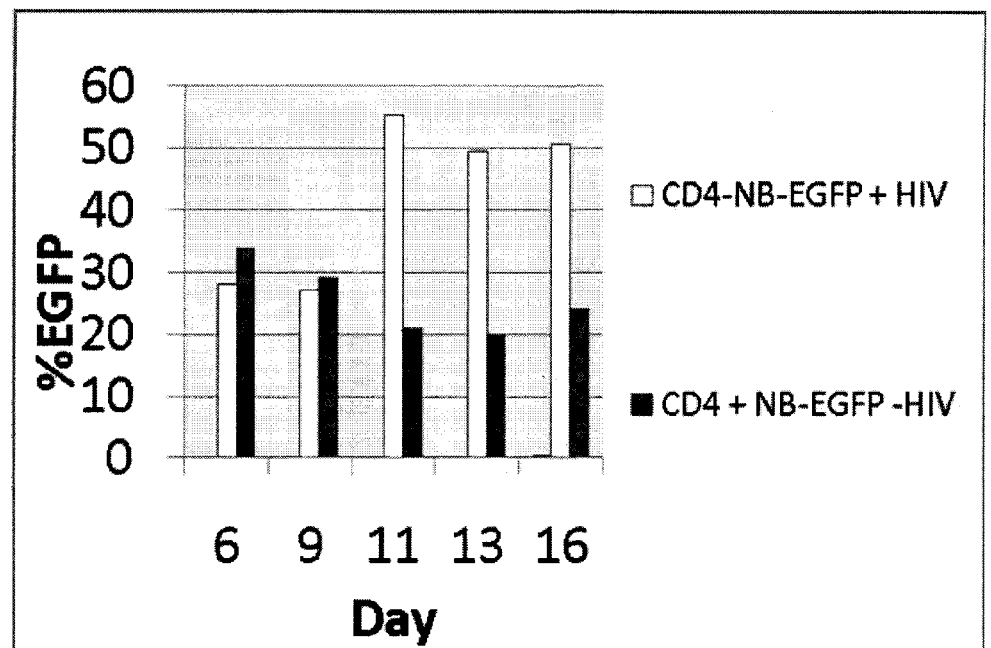

FIG. 11. Nullbasic conveys a selective advantage to primary human CD4 positive cells following HIV-1 infection. Primary human CD4 positive cells were isolated using CD4 microbeads and MAC columns for positive selection. The CD4 cells were activated with IL-2 and added to plate pre-coated with anti-CD3 and anti-CD28 antibodies. The activated cells were transduced with MoMLV vectors and the amount of Nullbasic-EGFP was determined by flow cytometry. The EGFP positive cells were infected with HIV-1 and cultured for 16 days and the amount of EGFP positive cells were determined again by Flow cytometry. In the absence of HIV-1, the relative level percentage of EFGP positive cells was similar at all time points. However when infected by HIV-1, the relative percentage of EGFP positive cells increased by 2-fold indicating that Nullbasic conveyed a selective advantage to CD4+ cells in the context of an HIV infection.

DETAILED DESCRIPTION OF THE INVENTION

The present invention has arisen after the inventor unexpectedly discovered that a mutant Tat protein ("Nullbasic") comprising a modified basic domain, and an amino acid sequence encoded by exon 2 of the Tat gene, is capable of potently inhibiting at least three different steps in the HIV-1 replication cycle. The inventor unexpectedly found that, in addition to inhibiting Tat-mediated transactivation, the mutant Tat protein suppressed Rev-mediated transport of HIV-1 mRNA. Furthermore, HIV-1 virions produced by cells expressing the mutant Tat protein had greatly reduced infectivity due to an at least partly reduced ability to undergo reverse transcription. As a result, cells expressing the mutant Tat protein described herein were protected against a spreading infection by HIV-1. This is a significant advancement over previously described Tat mutants, which are expressed at relatively lower levels and, at most, inhibit one step of the HIV-1 replication cycle (i.e. Tat-mediated transactivation). It will be appreciated that these novel findings highlight hitherto unrecognized activities of Tat and represent new avenues for therapeutic intervention.

Proteins

According to one aspect, the invention provides an isolated mutant Tat protein comprising (i) an amino acid sequence of (a) an activation domain, and (b) an amino acid sequence of a modified basic domain; and (ii) another amino acid sequence that is encoded by a nucleotide sequence of exon 2 of a Tat gene. The invention also provides a method of producing the isolated mutant Tat protein, which method includes the step of introducing one or more amino acid modifications into the basic domain to thereby produce the isolated mutant Tat protein.

In one embodiment, the amino acid sequence in (ii) comprises a glycine at a position corresponding to residue 79 of the amino acid sequence encoded by exon 2 of the Tat gene. Preferably, the amino acid sequence in (ii) comprises an RGD amino acid sequence, wherein the glycine is at a position corresponding to residue 79 of the amino acid sequence encoded by exon 2 of the Tat gene.

The Tat gene may be an HIV-1 Tat gene or an HIV-2 Tat gene. Suitably, the Tat gene is an HIV-1 Tat gene. It will be appreciated that the basic domain is encoded by a nucleotide sequence of exon 1 of the Tat gene, while the RGD amino acid sequence is encoded by a nucleotide sequence of exon 2 of the HIV-1 Tat gene.

For the purposes of this invention, by "isolated" is meant present in an environment removed from a natural state or otherwise subjected to human manipulation. Isolated material may be substantially or essentially free from components that normally accompany it in its natural state, or may be manipulated so as to be in an artificial state together with components that normally accompany it in its natural state. The term "isolated" also encompasses terms such as "enriched", "purified", "synthetic" and/or "recombinant".

By "protein" is meant an amino acid polymer. The amino acids may be natural or non-natural amino acids as are well understood in the art.

A "peptide" is a protein having no more than sixty (60) amino acids.

A polypeptide is a protein having more than sixty (60) amino acids.

The invention also provides fragment, variants, and derivatives of the isolated mutant Tat proteins of the invention.

Figure 1:
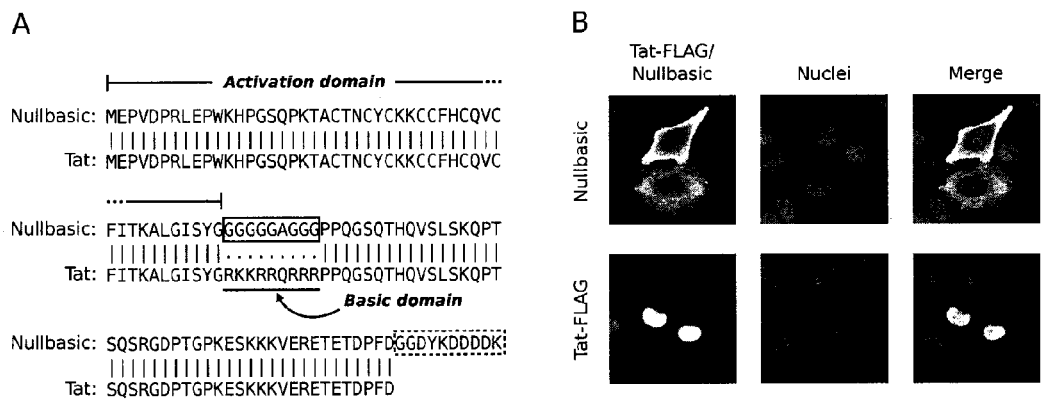
FIG. 1. Nullbasic is a HIV-1 Tat mutant that localizes to the cell cytoplasm. (A) Amino-acid sequence alignment of Nullbasic (upper rows; SEQ ID NO:1) against the BH10 clone of Tat (lower rows; SEQ ID NO:2). Vertical bars indicate amino acid identity and dots indicate engineered substitutions. The solid box highlights the engineered basic domain mutations in Nullbasic, while the dashed box indicates a FLAG epitope tag added to the carboxy terminal. (B) HeLa cells expressing Nullbasic (top row) or Tat-FLAG (bottom row) were visualized by confocal microscopy using anti-FLAG/FITC antibodies. Nuclei were stained with DAPI. Images are representative of 6 fields per slide from two independent experiments.

The terms "mutant", "mutation" and "mutated" are used herein to preferably encompass amino acid modifications of the basic domain of a mutant Tat protein. Suitably, said one or more amino acid modifications are amino acid substitutions, wherein one or more amino acids of the basic domain are substituted for, replaced by, or otherwise changed to, one or more non-basic amino acids. Suitably, said one or more non-basic amino acids are neutral amino acids. Thus, said one or more non-basic amino acids may be one or more glycine and/or alanine amino acids. In view of the foregoing, it will be appreciated that at least 1, at least 2, 3, 4, 5, 6, 7, 8 and up to 9 amino acids of the basic domain may be replaced by non-basic amino acids. It will also be appreciated that a plurality of amino acids (i.e. more than one (1)) of the basic domain are typically replaced by non-basic amino acids. Non-limiting examples include mutant Tat proteins wherein amino acids 52-57, or amino acids 49-57 of the basic domain have been substituted for, replaced by, or otherwise changed to, non-basic (e.g. neutral) amino acids. In one particularly preferred embodiment, the isolated mutant Tat protein comprises an amino acid sequence as set forth in FIG. 1 (SEQ ID NO:1).

A person of skill in the art will appreciate that mutant Tat proteins can be created by mutagenizing a protein or alternatively by mutagenizing an isolated nucleic acid encoding a protein, such as by random mutagenesis or site-directed mutagenesis. Examples of nucleic acid mutagenesis methods are provided in Chapter 9 of CURRENT PROTOCOLS IN MOLECULAR BIOLOGY, Ausubel et al., supra, chemical modification of proteins by hydroxylamine, incorporation of dNTP analogs into nucleic acids, PCR-based random mutagenesis such as described in Stemmer, 1994, Proc. Natl. Acad. Sci. USA 91 10747 or Shafikhani et al., 1997, Biotechniques 23 304, or mutagenesis kits such as Diversity™, and QuickChange™ are also contemplated by way of example.

Another example of how the mutant Tat protein may be prepared is provided in the Materials and Methods section of Example 1 contained herein.

The invention also provides fragments of the mutant Tat proteins. A protein "fragment" includes an amino acid sequence that constitutes less than 100%, but at least 20%, 30%, 40%, 50%, 60%, 70%, 80% or 90%, 92%, 94%, 96%, 98%, or 99% of said isolated mutant Tat protein.

In particular aspects, a protein fragment may comprise, for example, at least 10, 15, 20, 25, 30, 35, 40, 45, 50, 55, 60, 65, 70, 75, 80, 85, 90 or 95 contiguous
amino acids of said mutant Tat protein.

It will be appreciated that a peptide may be a protein fragment, for example comprising at least 10, preferably at least 15, 20, 25, 30, 35, 40, 45, and more preferably at least 50 contiguous amino acids.

Peptide fragments may be obtained through the application of standard recombinant nucleic acid techniques or synthesized using conventional liquid or solid phase synthesis techniques. For example, reference may be made to solution synthesis or solid phase synthesis as described, for example, in Chapter 18 of CURRENT PROTOCOLS IN PROTEIN SCIENCE, Coligan et al. Eds (John Wiley & Sons, 1995-2000). Alternatively, peptides can be produced by digestion of a mutant Tat protein of the invention with proteases such as endoLys-C, endoArg-C, endoGlu-C and staphylococcus V8-protease. The digested fragments can be purified by, for example, high performance liquid chromatographic (HPLC) techniques as are well known in the art.

It will also be appreciated that larger peptides and isolated mutant Tat proteins comprising a plurality of the same or different fragments are contemplated.

The invention also provides variants of the mutant Tat proteins.

As used herein, a protein "variant" shares a definable nucleotide or amino acid sequence relationship with an isolated protein of the invention. Preferably, protein variants share at least 70% or 75%, preferably at least 80% or 85% or more preferably at least 90%, 91%, 92%, 93%, 94%, 95%, 96%, 97%, 98% or 99% sequence identity with the amino acid sequences of the invention.

As used herein "variant" proteins of the invention have one or more amino acids deleted or substituted by different amino acids. It is well understood in the art that some amino acids may be substituted or deleted without changing the activity of the mutant Tat protein (conservative substitutions).

The term "variant" also includes isolated proteins of the invention produced from, or comprising amino acid sequences of, allelic variants.

Terms used generally herein to describe sequence relationships between respective proteins and nucleic acids include "comparison window", "sequence identity", "percentage of sequence identity" and "substantial identity". Because respective nucleic acids/proteins may each comprise (1) only one or more portions of a complete nucleic acid/protein sequence that are shared by the nucleic acids/proteins, and (2) one or more portions which are divergent between the nucleic acids/proteins, sequence comparisons are typically performed by comparing sequences over a "comparison window" to identify and compare local regions of sequence similarity. A "comparison window" refers to a conceptual segment of typically 6, 9 or 12 contiguous residues that is compared to a reference sequence. The comparison window may comprise additions or deletions (i.e., gaps) of about 20% or less as compared to the reference sequence for optimal alignment of the respective sequences. Optimal alignment of sequences for aligning a comparison window may be conducted by computerised implementations of algorithms (Geneworks program by Intelligenetics; GAP, BESTFIT, FASTA, and TFASTA in the Wisconsin Genetics Software Package Release 7.0, Genetics Computer Group, 575 Science Drive Madison, Wis., USA, incorporated herein by reference) or by inspection and the best alignment (i.e. resulting in the highest percentage homology over the comparison window) generated by any of the various methods selected. Reference also may be made to the BLAST family of programs as for example disclosed by Altschul et al., 1997, Nucl. Acids Res. 25 3389, which is incorporated herein by reference. A detailed discussion of sequence analysis can be found in Unit 19.3 of CURRENT PROTOCOLS IN MOLECULAR BIOLOGY Eds. Ausubel et al. (John Wiley & Sons Inc NY, 1995-1999).

The term "sequence identity" is used herein in its broadest sense to include the number of exact nucleotide or amino acid matches having regard to an appropriate alignment using a standard algorithm, having regard to the extent that sequences are identical over a window of comparison. Thus, a "percentage of sequence identity" is calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence identity. For example, "sequence identity" may be understood to mean the "match percentage" calculated by the DNASIS computer program (Version 2.5 for windows; available from Hitachi Software engineering Co., Ltd., South San Francisco, Calif., USA).

Derivatives of the mutant Tat proteins are also provided.

As used herein, "derivative" proteins have been altered, for example by conjugation or complexing with other chemical moieties, by post-translational modification (e.g. phosphorylation, acetylation and the like), modification of glycosylation (e.g. adding, removing or altering glycosylation) and/or inclusion of additional amino acid sequences as would be understood in the art.

Additional amino acid sequences may include fusion partner amino acid sequences which create a fusion protein. By way of example, fusion partner amino acid sequences may assist in detection and/or purification of the isolated fusion protein. Non-limiting examples include metal-binding (e.g. polyhistidine) fusion partners, maltose binding protein (MBP), Protein A, glutathione S-transferase (GST), fluorescent protein sequences (e.g. GFP), epitope tags such as myc, FLAG and haemagglutinin tags.

Other derivatives contemplated by the invention include, but are not limited to, modification to side chains, incorporation of unnatural amino acids and/or their derivatives during peptide, or protein synthesis and the use of crosslinkers and other methods which impose conformational constraints on the mutant Tat proteins, fragments and variants of the invention.

Nucleic Acids

Another aspect of the invention provides an isolated nucleic acid that encodes an isolated mutant Tat protein of the invention, inclusive of fragments variants and derivatives thereof.

The term "nucleic acid" as used herein designates single- or double-stranded DNA and RNA. DNA includes genomic DNA and cDNA. RNA includes mRNA, RNA, RNAi, siRNA, cRNA and autocatalytic RNA. Nucleic acids may also be DNA-RNA hybrids. A nucleic acid comprises a nucleotide sequence which typically includes nucleotides that comprise an A, G, C, T or U base. However, nucleotide sequences may include other bases such as inosine, methylycytosine, methylinosine, methyladenosine and/or thiouridine, although without limitation thereto.

A "polynucleotide" is a nucleic acid having eighty (80) or more contiguous nucleotides, while an "oligonucleotide" has less than eighty (80) contiguous nucleotides.

A "probe" may be a single or double-stranded oligonucleotide or polynucleotide, suitably labeled for the purpose of detecting complementary sequences in Northern or Southern blotting, for example.

A "primer" is usually a single-stranded oligonucleotide, preferably having 15-50 contiguous nucleotides, which is capable of annealing to a complementary nucleic acid "template" and being extended in a template-dependent fashion by the action of a DNA polymerase such as Taq polymerase, RNA-dependent DNA polymerase or Sequenase™.

Another particular aspect of the invention provides a variant of an isolated nucleic acid that encodes an isolated protein of the invention.

In one embodiment, nucleic acid variants encode a variant of an isolated protein of the invention.

In another embodiment, nucleic acid variants share at least 60% or 65%, 66%, 67%, 68%, 69%, preferably at least 70%, 71%, 72%, 73%, 74% or 75%, more preferably at least 80%, 81%, 82%, 83%, 84%, or 85%, and even more preferably at least 90%, 91%, 92%, 93%, 94%, or 95% nucleotide sequence identity with an isolated nucleic acid of the invention.

Typically, complementary nucleotide sequences are identified by blotting techniques that include a step whereby nucleotides are immobilized on a matrix (preferably a synthetic membrane such as nitrocellulose), a hybridization step, and a detection step, typically using a labelled probe or other complementary nucleic acid. Southern blotting is used to identify a complementary DNA sequence; Northern blotting is used to identify a complementary RNA sequence. Dot blotting and slot blotting can be used to identify complementary DNA/DNA, DNA/RNA or RNA/RNA polynucleotide sequences. Such techniques are well known by those skilled in the art, and have been described in Ausubel et al., supra, at pages 2.9.1 through 2.9.20. According to such methods, Southern blotting involves separating DNA molecules according to size by gel electrophoresis, transferring the size-separated DNA to a synthetic membrane, and hybridizing the membrane bound DNA to a complementary nucleotide sequence. An alternative blotting step is used when identifying complementary nucleic acids in a cDNA or genomic DNA library, such as through the process of plaque or colony hybridization. Other typical examples of this procedure is described in Chapters 8-12 of Sambrook et al., supra.

Methods for detecting labeled nucleic acids hybridized to an immobilized nucleic acid are well known to practitioners in the art. Such methods include autoradiography, chemiluminescent, fluorescent and colorimetric detection.

Nucleic acids may also be isolated, detected and/or subjected to recombinant DNA technology using nucleic acid sequence amplification techniques.

Suitable nucleic acid amplification techniques are well known to the skilled addressee, and include polymerase chain reaction (PCR); strand displacement amplification (SDA); rolling circle replication (RCR); nucleic acid sequence-based amplification (NASBA), Q-$\beta$ replicase amplification and helicase-dependent amplification, although without limitation thereto.

As used herein, an "amplification product" refers to a nucleic acid product generated by nucleic acid amplification.

Nucleic acid amplification techniques may include particular quantitative and semi-quantitative techniques such as qPCR, real-time PCR and competitive PCR, as are well known in the art.

Genetic Constructs

Another aspect of the invention provides a genetic construct that comprises an isolated nucleic acid of the invention operably linked to one or more additional nucleotide sequences.

Suitably, the genetic construct is in the form of, or comprises genetic components of, a plasmid, bacteriophage, a cosmid, a yeast or bacterial artificial chromosome as are well understood in the art. Genetic constructs may be suitable for maintenance and propagation of the isolated nucleic acid in bacteria or other host cells, for manipulation by recombinant DNA technology and/or expression of the nucleic acid or an encoded protein of the invention.

For the purposes of host cell expression, the genetic construct is an expression construct. Suitably, the expression construct comprises the nucleic acid of the invention operably linked to one or more additional sequences in an expression vector. An "expression vector" may be either a self-replicating extra-chromosomal vector such as a plasmid, or a vector that integrates into a host genome. Non-limiting examples of expression constructs include adenovirus vectors, adeno-associated virus vectors, herpesviral vectors, retroviral vectors, lentiviral vectors, and the like. For example, adenovirus vectors can be first, second, third, and/or fourth generation adenoviral vectors or gutless adenoviral vectors. Adenovirus vectors can be generated to very high titers of infectious particles, infect a great variety of cells, efficiently transfer genes to cells that are not dividing, and are seldom integrated in the host genome, which avoids the risk of cellular transformation by insertional mutagenesis (Douglas and Curiel, *Science and Medicine*, March/April 1997, pages 44-53; Zern and Kresinam, *Hepatology* 25:484-91, 1997). Representative adenoviral vectors are described by Stratford-Perricaudet et al. (*J. Clin. Invest.* 90:626-30, 1992), Graham and Prevec (In Methods in Molecular Biology: Gene Transfer and Expression Protocols 7:109-28, 1991) and Barr et al. (*Gene Therapy*, 2:151-55, 1995).

Adeno-associated virus (AAV) vectors also are suitable for administration of the nucleic acids of the invention. Methods of generating AAV vectors, administration of AAV vectors and their uses are well known in the art (see, e.g., U.S. Pat. No. 6,951,753; U.S. Patent Application Publication Nos. 2007/036757, 2006/205079, 2005/163756, 2005/002908; and PCT Publication Nos. WO 2005/116224 and WO 2006/119458).

Suitable herpesvirus vectors can be derived from any one of a number of different types of herpesviruses, including, but not limited to, herpes simplex virus-1 (HSV-1), HSV-2 and herpesvirus saimiri. Recombinant herpesvirus vectors, their construction and uses are well and described in the art (see, e.g., U.S. Pat. Nos. 6,951,753; 6,379,674; 6,613,892; 6,692,955; 6,344,445; 6,319,703; and 6,261,552; and U.S. Patent Application Publication No. 2003/0083289).

Retrovirus vectors, including lentivirus vectors, can also be used with the compositions and methods described herein. Lentiviruses include, but are not limited to, human immunodeficiency virus (such as HIV-1 and HIV-2), feline immunodeficiency virus, equine infectious anemia virus, and simian immunodeficiency virus. Other retroviruses include, but are not limited to, human T-lymphotropic virus, simian T-lymphotropic virus, murine leukemia virus, bovine leukemia virus, and feline leukemia virus. Methods of generating retrovirus and lentivirus vectors and their uses have been well described in the art (see, e.g., U.S. Pat. Nos. 7,211,247; 6,979,568; 7,198,784; 6,783,977; and 4,980,289).

In one particular embodiment, the expression construct is a non-lentiviral retroviral construct. Suitably, said construct is a Murine leukaemia virus (MLV)-based retroviral vector. It will be appreciated that inhibition of HIV replication may be improved by expressing the mutant Tat protein using an MLV-based retroviral construct as well as a lentiviral retroviral construct.

By "operably linked" is meant that said additional nucleotide sequence(s) is/are positioned relative to the nucleic acid of the invention preferably to initiate, regulate or otherwise control transcription.

In one embodiment, the additional nucleotide sequences are regulatory sequences. Regulatory nucleotide sequences will generally be appropriate for the host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences.

Constitutive or inducible promoters as known in the art are contemplated by the invention. The promoters may be either naturally occurring promoters, or hybrid promoters that combine elements of more than one promoter. Non-limiting examples of promoters include SV40, cytomegalovirus (CMV), and HIV-1 LTR promoters.

In another embodiment, the additional nucleotide sequence is a selectable marker gene to allow the selection of transformed host cells. Selectable marker genes are well known in the art and will vary with the host cell used.

The expression construct may also include an additional nucleotide sequence encoding a fusion partner (typically provided by the expression vector) so that the recombinant mutant Tat protein of the invention is expressed as a fusion protein, as hereinbefore described.

Host Cells and Methods of Production

In further aspects, the invention provides host cells comprising genetic construct that encode the mutant Tat protein. Suitable host cells for expression may be prokaryotic or eukaryotic. For example, suitable host cells may be mammalian cells (e.g. HeLa, HEK293T, Jurkat cells), yeast cells (e.g. *Saccharomyces cerevisiae*), insect cells (e.g. Sf9, *Trichoplusia ni*) utilized with or without a baculovirus expression system, or bacterial cells, such as *E. coli*, or a *Vaccinia* virus host. Introduction of genetic constructs into host cells (whether prokaryotic or eukaryotic) is well known in the art, as for example described in CURRENT PROTOCOLS IN MOLECULAR BIOLOGY Eds. Ausubel et al., (John Wiley & Sons, Inc. 1995-2009), in particular Chapters 9 and 16.

The recombinant protein may be conveniently prepared by a person skilled in the art using standard protocols as for example described in Sambrook, et al., MOLECULAR CLONING. A Laboratory Manual (Cold Spring Harbor Press, 1989), in particular Sections 16 and 17; CURRENT PROTOCOLS IN MOLECULAR BIOLOGY Eds. Ausubel et al., (John Wiley & Sons, Inc. 1995-2009), in particular Chapters 10 and 16; and CURRENT PROTOCOLS IN PROTEIN SCIENCE Eds. Coligan et al., (John Wiley & Sons, Inc. 1995-2009), in particular Chapters 1, 5 and 6.

For the particular purpose of fusion mutant Tat protein purification by affinity chromatography, relevant matrices for affinity chromatography are glutathione-, amylose-, anti-FLAG-, and nickel- or cobalt-conjugated resins respectively. Many such matrices are available in "kit" form, such as the QIAexpress™ system (Qiagen) useful with ($HIS_6$) fusion partners, the Pharmacia GST purification system and the Sigma-Aldrich FLAG Affinity gels.

Preferably, the fusion partners also have protease cleavage sites, such as for Factor $X_a$ or Thrombin, which allow the relevant protease to partially digest the fusion mutant Tat protein of the invention and thereby liberate the recombinant mutant Tat protein of the invention therefrom. The liberated mutant Tat protein can then be isolated from the fusion partner by subsequent chromatographic separation.

Isolated proteins of the invention (inclusive of fragments, derivatives and variants) may be prepared by any suitable procedure known to those of skill in the art. Preferably, the isolated protein is a recombinant protein.

By way of example only, a recombinant isolated protein of the invention may be produced by a method including the steps of:
 (i) preparing an expression construct which comprises an isolated nucleic acid of the invention, operably linked to one or more regulatory nucleotide sequences;
 (ii) transfecting or transforming a suitable host cell with the expression construct;
 (iii) expressing a recombinant protein in said host cell; and
 (iv) isolating the recombinant protein from said host cell.

Pharmaceutical Compositions and Therapy

Further aspects of the invention provide prophylactic and therapeutic methods and/or pharmaceutical compositions for treating an HIV infection (e.g. an HIV-1 infection), and/or alleviating symptoms associated therewith, in a host (e.g. a human).

In one particular aspect, a method of preventing or treating an HIV infection in a host includes the step of administering to the host a therapeutic agent selected from the group consisting of:
 (i) an isolated protein of the invention, inclusive of variants, derivatives and fragments thereof;
 (ii) an isolated nucleic acid of the invention, inclusive of variants, derivatives and fragments thereof;
 (iii) an expression construct encoding the isolated nucleic acid of (ii);
 (iv) a host cell comprising the expression construct of (iii); and/or
 (v) a pharmaceutical composition comprising one or more of (i)-(iv), to thereby prevent or treat said HIV infection (e.g. an HIV-1 infection) in said host.

Suitably, the therapeutic agent is capable of at least partly alleviating one or more symptoms associated with the HIV infection. Preferably, the host is a human.

In another aspect, the invention provides a method of administering the therapeutic agent into a host, to at least partly inhibit, suppress, or otherwise reduce Tat-mediated transactivation in said host, or in one or more cells and/or tissues of said host.

In yet another aspect, the invention provides a method of administering the therapeutic agent into a host, to at least partly inhibit, suppress, or otherwise reduce Rev-mediated transport of HIV-1 mRNA in said host, or in one or more cells and/or tissues of said host.

In still yet another aspect, the invention provides a method of administering the therapeutic agent into a host, to at least partly inhibit, suppress, or otherwise reduce HIV-1 virion production and/or infectivity in said host, or in one or more cells and/or tissues of said host.

The aforementioned methods may include a step that comprises adoptive cell therapy, such as adoptive T cell therapy.

The skilled addressee will appreciate that, in particular embodiments (i.e. in cases when retroviral vectors or recombinant HIV vectors are used), it may be desirable to: (i) harvest patient cells (e.g. T-cells, T-cell progenitors such as bone marrow stem cells, or other lymphoid progenitors); (ii) infect the patient cells in tissue culture ex vivo; and (iii) infuse the transfected cells into the patient. Such a procedure may be particularly suitable for HIV patients that have failed to respond to HIV therapy in the past and will be given a transplant as the cells expressing the mutant Tat protein may be transferred into the patient during the transplant surgery.

Suitably, the pharmaceutical composition comprises a pharmaceutically-acceptable carrier, diluent or excipient.

By "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, 1991) which is incorporated herein by reference.

Any safe route of administration may be employed for administering the mutant Tat protein of the invention. For example, oral, rectal, parenteral, sublingual, buccal, intravenous, intra-articular, intra-muscular, intra-dermal, subcutaneous, inhalational, intraocular, intraperitoneal, intracerebroventricular, transdermal and the like may be employed.

Dosage forms include tablets, dispersions, suspensions, injections, solutions, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be achieved by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be achieved by using other polymer matrices, liposomes and/or microspheres.

Pharmaceutical compositions of the present invention suitable for oral or parenteral administration may be presented as discrete units such as capsules, sachets or tablets each containing a pre-determined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more therapeutic agents as described above with the carrier which constitutes one or more necessary ingredients. In general, the compositions are prepared by uniformly and intimately admixing the therapeutic agents of the invention with liquid carriers or finely divided solid carriers or both, and then, if necessary, shaping the product into the desired presentation.

The above compositions may be administered in a manner compatible with the dosage formulation, and in such amount as is effective to prophylactically and/or therapeutically treat an HIV infection and/or alleviate symptoms associated therewith. The dose administered to a patient, in the context of the present invention, should be sufficient to achieve a beneficial response in a patient over time such as a reduction in the level of HIV virus, or to inhibit infection by the HIV virus. The quantity of the therapeutic agent(s) to be administered may depend on the subject to be treated inclusive of the age, sex, weight and general health condition thereof. In this regard, precise amounts of the therapeutic agent(s) required to be administered will depend on the judgement of the clinician.

In determining the effective amount of the therapeutic agent to be administered in the treatment or prophylaxis against HIV-1, the clinician may evaluate circulating plasma levels, and progression of the HIV-1 infection. In any event, suitable dosages of the therapeutic agents of the invention may be readily determined by those skilled in the art. Such dosages may be in the order of nanograms to milligrams of the therapeutic agents of the invention.

Antibodies

The invention also contemplates antibodies raised against and which bind the isolated mutant Tat proteins, fragments, variants, and derivatives of the invention. Antibodies of the invention may be polyclonal or monoclonal, native or recombinant. Well-known protocols applicable to antibody production, purification and use may be found, for example, in Chapter 2 of Coligan et al., CURRENT PROTOCOLS IN IMMUNOLOGY (John Wiley & Sons NY, 1991-1994) and Harlow, E. & Lane, D. *Antibodies: A Laboratory Manual*, Cold Spring Harbor, Cold Spring Harbor Laboratory, 1988, which are both herein incorporated by reference.

Generally, antibodies of the invention bind to or conjugate with an isolated protein, fragment, variant, or derivative of the invention. For example, the antibodies may be polyclonal antibodies. Such antibodies may be prepared for example by injecting an isolated protein, fragment, variant or derivative of the invention into a production species, which may include mice or rabbits, to obtain polyclonal antisera. Methods of producing polyclonal antibodies are well known to those skilled in the art. Exemplary protocols which may be used are described for example in Coligan et al., CURRENT PROTOCOLS IN IMMUNOLOGY, supra, and in Harlow & Lane, 1988, supra.

Monoclonal antibodies may be produced using the standard method as for example, described in an article by Köhler & Milstein, 1975, Nature 256, 495, which is herein incorporated by reference, or by more recent modifications thereof as for example, described in Coligan et al., CURRENT PROTOCOLS IN IMMUNOLOGY, supra by immortalizing spleen or other antibody producing cells derived from a production species which has been inoculated with one or more of the isolated proteins, fragments, variants or derivatives of the invention.

The invention also includes within its scope antibody fragments, such as Fc, Fab or F(ab)$_2$ fragments of the polyclonal or monoclonal antibodies referred to above. Alternatively, the antibodies may comprise single chain Fv antibodies (scFvs) against the peptides of the invention. Such scFvs may be prepared, for example, in accordance with the methods described respectively in U.S. Pat. No. 5,091,513, European Patent No 239,400 or the article by Winter & Milstein, 1991, Nature 349 293, which are incorporated herein by reference Antibodies and antibody fragments of the invention may be particularly suitable for affinity chromatography purification of the mutant Tat proteins described herein. For example reference may be made to affinity chromatographic procedures described in Chapter 9.5 of Coligan et al., CURRENT PROTOCOLS IN IMMUNOLOGY, supra.

The host may be any animal, inclusive of mammals such as domestic animals, livestock, performance animals and humans. Preferably, the host is a human.

In order that the invention may be readily understood and put into practical effect, particular preferred embodiments will now be described by way of the following non-limiting examples.

EXAMPLE 1

Materials & Methods

Cell Culture and Transfections.

HeLa and HEK293T cells were cultured in RPMI 1640 medium supplemented with 100 U/ml penicillin, 100 mg/ml streptomycin and 10% (v/v) newborn bovine serum (Invitrogen Corporation). HeLa-CD4-LTR-β-gal (MAGI) cells (Kimpton & Emerman, 1992) were obtained from Michael Emerman through the NIH AIDS Research and Reference Reagent Program, Division of AIDS, NIAID, NIH. The cells were maintained in the same medium as above but supplemented with 0.2 mg/ml G418 and 0.1 mg/ml hygromycin B. All cells were incubated at 37° C. under a humidified atmosphere of 5% $CO_2$ in air. Transfections were performed with Lipofectamine 2000 (Invitrogen) or FuGENE 6 (Roche Diagnostics Corporation) transfection reagents according to the manufacturers' instructions. Transfections were performed in 6-cm dishes for reporter assays and Western blotting, and 10-cm dishes for HIV-1 virion production.

Plasmids.

The plasmid expressing the two-exon, 101 amino-acid, BH10 clone of Tat fused to the FLAG epitope (pcDNA3.1/Tat-FLAG) was a gift from Monsef Benkirane, Institut de Génétique Humaine, France. Nullbasic was created by firstly removing the basic domain sequence (corresponding to amino acids 49-57 in Tat) in pcDNA3.1/Tat-FLAG by inverse PCR before complementary oligonucleotides encoding the amino acid sequence, Gly-Gly-Gly-Gly-Gly-Ala-Gly-Gly-Gly (SEQ ID NO:3) were annealed and ligated to form pcDNA3.1/Nullbasic. Correct orientation of the insert was determined by DNA sequencing. To create the Nullbasic-EGFP-encoding lentivector pLOX-CW/Nullbasic-EGFP, the EGFP gene from pIRES2-EGFP (Clontech Laboratories) was cloned onto the 39 end of Nullbasic before the Nullbasic-EGFP cassette was subcloned to replace gfp in pLOX-CWgfp (Salmon et al., 2000) using Bam HI and Sal I restriction sites. The Tat-transactivation luciferase reporter pGL3-LTR consists of the long terminal repeat from HIV-1 clone SF2 cloned into pGL3-basic (Promega Corporation) via Bam HI and Hind III restriction enzyme sites. The LTR spans nucleotides 2180 to +81, relative to the start of transcription. A Rev-independent Env expression construct, pNL1.5E-RTEm26CTE (Smulevitch et al., 2006), was a gift from Barbara Felber, National Cancer Institute, Maryland, USA. The Env-RTEm26CTE open reading frame was subcloned to replace the HIV-1 genome in pGCH using Bss HI and Xho I restriction enzymes, thus forming pGCH-Env-RTEm26CTE. The Rev independent Gag expression construct pCMV5-Gag (Tritel & Resh, 2000) was a gift from Marilyn Resh and George Pavlakis, National Cancer Institute, Maryland, USA. The FLAG epitope sequence was added to the 39 end of gag by inverse PCR mutagenesis. A plasmid expressing the BRU clone of Rev (pRSV-Rev) was a gift from Damian Purcell, University Melbourne, Australia. The MYC epitope sequence was added to the 59 end of rev by inverse PCR mutagenesis before the Myc-Rev cassette was subcloned into pcDNA3.1+ (Invitrogen). The β-galactosidase expression plasmid pCMVb (MacGregor & Caskey, 1989) was used as a transfection control in various experiments as indicated. β-galactosidase activity was measured by the chlorophenol red-β-D-galactopyranoside (CPRG)-based assay (Eustice et al., 1991).

Indirect Immunofluorescence.

HeLa cells were grown on coverslips and transfected with plasmids as above. Cells were fixed 24 h later in 3% (w/v) paraformaldehyde, quenched with 50 mM NH4Cl, permeabilized with 0.1% (v/v) Triton X-100 and blocked in 10% (v/v) normal goat serum (Millipore Corporation). Tat-FLAG and Nullbasic were probed with mouse anti-FLAG M2 monoclonal antibody (Sigma-Aldrich Incorporated) and FITC-conjugated goat antimouse antibody (Invitrogen). Myc-Rev was probed with rabbit anti-MYC polyclonal antibody (Cell Signaling Technology Incorporated) and Cy3-conjugated goat anti-rabbit antibody (Invitrogen). Nuclei were stained with 1 mM 49,6-diamidino-2-phenylindole (DAPI; Invitrogen) and coverslips were mounted onto slides with SlowFade Gold mounting medium (Invitrogen). Images were acquired with a Leica TCS SP2 confocal system (Leica Microsystems) using an oil-immersion 636 objective lens and standard lasers and filters for FITC, Cy3 and DAPI (two photon) fluorescence.

Transactivation Assay.

HeLa cells were co-transfected with 200 ng of Tat-FLAG, 500 ng of pGL3-LTR, 300 ng of pCMVb and either 200 ng, 2 mg or 4 mg of Nullbasic plasmid. Cells were harvested 24 h posttransfection and cell lysates prepared with phosphate-buffered saline (PBS) containing 0.5% (w/v) Triton X-100 and protease inhibitors (Roche). Lysates were assayed for luciferase activity using the Steady-Glo luciferase assay system (Promega). β-galactosidase activity was assayed as above.

HIV-1 Virion Infectivity.

For the effect of Nullbasic on virion infectivity experiment, HEK293T cells were transfected with 5 mg of pGCH provirus and either 4 mg or 8 mg of Nullbasic or Tat-FLAG plasmids. Supernatants were collected 48 h post-transfection, filtered through 0.45 mm filters and virion concentrations were determined by RT colorimetric assay (Roche). MAGI cells were infected with 20 ng RTequivalent of virions for 2 h and allowed to incubate for a further 46 h. Cells were then lysed and assayed for β-galactosidase expression using the CPRG assay (Eustice et al., 1991). Total cellular protein amounts were measured using the Bradford assay (Bradford, 1976), and was used to normalise β-galactosidase expression. For the effect of Nullbasic on viral CA and RT levels experiment, HEK293T cells were transfected with 5 mg of pGCH and either 4 mg or 8 mg of Tat-FLAG or Nullbasic plasmids. Viral supernatants were collected 48 h post-transfection, filtered, and CA and RT concentrations were determined by ELISA (Zeptometrix Corporation) and colorimetric enzyme assay (Roche), respectively.

Western Blot.

For the Western blotting of cell lysates, HEK293T cells were transfected with either 5 mg of pGCH provirus, 1.5 mg of pGCHEnv-RTEm26CTE or 2 mg of pCMV5-Gag-FLAG. Cells were also co-transfected with 250 ng of pCMVb and either Tat-FLAG or Nullbasic plasmids as indicated. Cells were lysed 24 h posttransfection and assayed for β-galactosidase and total protein concentrations as above. Lysates equivalent in β-galactosidase activity were boiled in sample buffer and electrophoresed in a sodium dodecylsulfate-containing polyacrylimide gel according to the methods of King and Laemmli (1971). Proteins were electroblotted to a polyvinylidene difluoride (PVDF) membrane (GE Healthcare) using a semi-dry transfer system (Bio-Rad). Tat-FLAG, Nullbasic and Gag-FLAG were detected with mouse anti-FLAG M2 monoclonal antibody (Sigma-Aldrich). HIV-1 Env and SU were detected with mouse anti-gp120 monoclonal antibody (a gift from Andy Poumbourios, Burnet Institute, Australia). Other HIV-1 proteins were detected with HIV-IG anti-serum (AIDS Research and Reference Reagent Program, Division of AIDS, NIAID, NIH). Mouse primary antibodies were detected with horseradish peroxidase (HRP)-conjugated goat anti-mouse antibody (Invitrogen), and HIV anti-serum was detected with HRP-conjugated goat anti-human IgG anti-serum (Sigma-Aldrich).

Virion RNA Packaging Assay.

HEK293T cells were co-transfected with 5 mg of pGCH provirus and 4 mg of either Tat-FLAG or Nullbasic plasmids. Culture supernatants were harvested and treated with DNase I to remove contaminating plasmid DNA before being ultracentrifuged through a 20% (v/v) sucrose cushion at 100 0006 g for 2 h. Packaged RNA from the virion pellets were extracted with TRIzol reagent (Invitrogen) before being reverse transcribed with random hexamers and Superscript III MMLV RT (Invitrogen) according to the manufacturer's instructions. cDNA was measured by quantitative PCR with Platinum SYBR Green qPCR supermix (Invitrogen) on the Rotor-Gene 6000 (Corbett Life Science) using primers, 59-TCT CTA GCA GTG GCG CCC GAA CAG GG (SEQ ID NO:4) and 59-GTC GCC GCC CCT CGC CTC TTG (SEQ ID NO:5). To control for reaction efficiency, kanamycin cassette control RNA (Promega) was added to the extracted RNA mixture and assayed as above with primers, 59-GGC TCG CGA TAA TGT CGG G (SEQ ID NO:6) and 59-GAT GGT CGG AAG AGG C (SEQ ID NO:7). Quantitated kanamycin cDNA levels were used to normalise viral cDNA levels.

Northern Blot and RNA Splicing Assay.

HEK293T cells were transfected with 5 mg of pGCH provirus and 4 mg or 8 mg of either Tat-FLAG or Nullbasic plasmids. Total RNA was extracted 48 h post-transfection using TRIzol reagent (Invitrogen) according to the manufacturer's instructions. Twenty micrograms of RNA samples were electrophoresed in a 1% (w/v) agarose gel containing 0.6 M formaldehyde and either stained with ethidium bromide to visualize ribosomal RNA, or blotted to a nitrocellulose membrane using a TurboBlotter transfer system (Schleicher and Schuell). RNAs were cross-linked to the membrane with ultraviolet light and heat, and HIV-1 mRNA species were detected with a 32P-labelled probe corresponding to the Bam HI-Xho I fragment in the 39 LTR of HIV-1. Hybridizations were visualized with a Typhoon 8600 imager (GE Healthcare). For the RNA splicing assay, total RNA obtained for the Northern analysis was used as a template for quantitative RTPCR as described above. The primers used to detect unspliced, singly-spliced and multiply-spliced viral mRNA have been previously described (Arrigo et al., 1990). Kanamycin cassette control RNA, as described above, was included in the assay to normalise for reaction efficiency.

Rev Reporter Assay.

HEK293T cells were transfected with either 1 mg of pGCH or 20 ng of pcDNA3.1/Myc-Rev, along with 100 ng of pDM128, 100 ng of pCMVb and 1.5 mg of either Nullbasic or empty vector (pcDNA3.1+) plasmids. Cells were harvested and lysed 24 h posttransfection before CAT expression was assayed by ELISA (Roche) according to the manufacturer's instructions. β-galactosidase activity was assayed as above. Establishment of the MAGI/Nullbasic-EGFP Cell Line Pseudotyped lentivirus particles were generated by co-transfecting HEK293T cells with pLOX-CW/Nullbasic-EGFP or pLOXCWgfp along with pCMVDR8.91 (Zufferey et al., 1997) and pHEF-VSV-G (a gift from Sabine Piller, Westmead Millennium Institute, Australia). MAGI cells were transduced with lentivirus particles in the presence of hexadimethrine bromide (8 mg/ml; Sigma-Aldrich) for 48 h before transduction was confirmed by fluorescence microscopy. Highly expressing cells were isolated by FACS using a MoFlo cell sorter (Beckman Coulter Incorporated), and expression of Nullbasic was confirmed by Western blot analysis.

Flow Cytometry of Cell-Surface Receptor Levels.

MAGI/Nullbasic-EGFP and non-transduced MAGI cells were incubated with mouse anti-CD4 or mouse anti-CXCR4 monoclonal antibodies (R&D Systems) followed by Cy5-conjugated goat anti-mouse antibody (Invitrogen). Receptor levels were quantitated by measuring Cy5 fluorescence using a FACScalibur flow cytometer (Becton Dickinson), counting 105 cells per sample.

Detergent-Free Endogenous Reverse Transcription Assay.

HIV-1 virions from HEK293T cells co-transfected with 5 μg of pGCH provirus and 4 μg of either Tat-FLAG or Nullbasic plasmids were assayed for endogenous (intravirion) reverse transcription as previously described (Warrilow et al., 2008). Virions were normalized for equivalent RT activity before assay. The primers used to quantitate minus-strand strong-stop DNA were 59-GGG TCT CTC TGG TTG ACC AGA (SEQ ID NO:8) and 59-ACA CAA CAG ACG GGC ACA CAC (SEQ ID NO:9).

Viral Replication Kinetics.

MAGI/Nullbasic-EGFP, MAGI/EGFP and non-transduced MAGI cells were infected with high doses (500 ng CA-equivalent) of pGCH-derived HIV-1 for 2 h. Non-adsorbed virions were removed by washing cells with PBS before infected cells were incubated for a 14-day period. Culture supernatants were periodically sampled for virion production by CA ELISA in triplicate.

Statistical Analyses.

Hartley's Fmax test was used to determine variance homoscedasticity between data sets. Student's t-test was used to evaluate null hypotheses for homoscedastic data, while Welch's t-test was used for heteroscedastic data. The underlying distributions were two tailed for all tests and significant difference was defined as p, 0.05.

Results

Nullbasic Is a Transdominant Tat Mutant.

Figure 2:
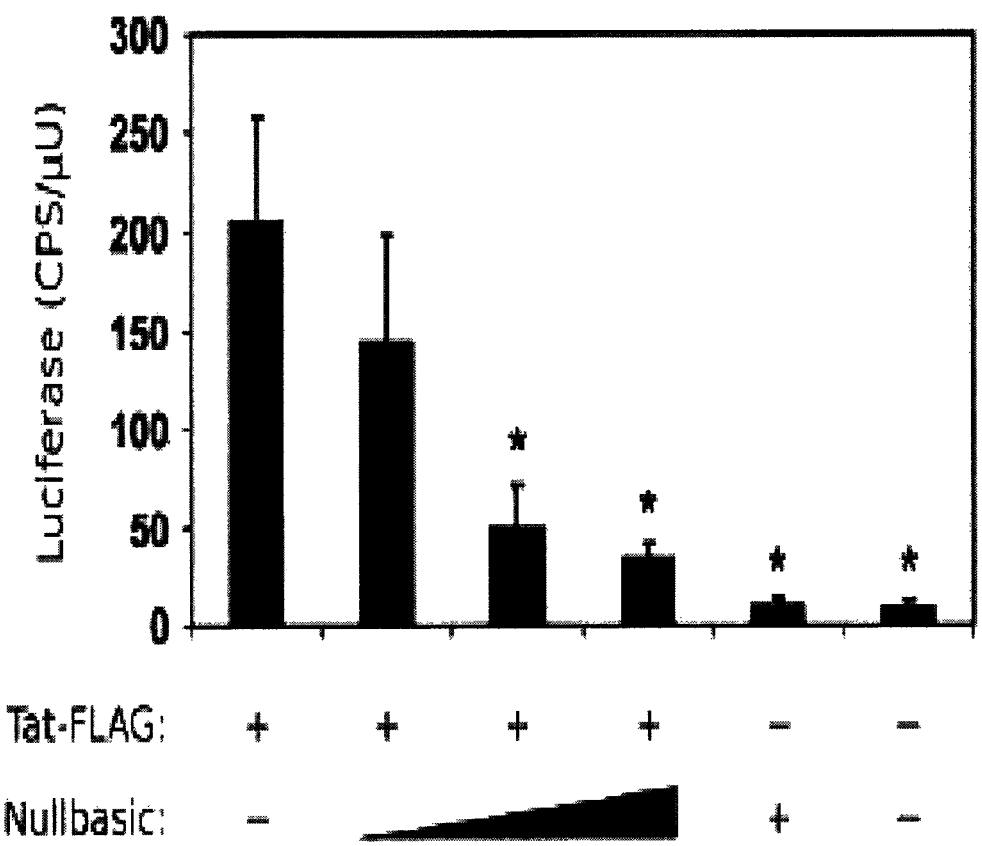
FIG. 2. Nullbasic inhibits Tat-mediated transactivation. Increasing amounts (200 ng, 2 mg and 4 mg) or Nullbasic expression vector were titrated into cells co-transfected with constant amounts of Tat-FLAG plasmid, a luciferase reporter of Tat transactivation (HIV-1 LTR promoter) and a constitutive galactosidase expression plasmid (CMV promoter). Luciferase values (CPS, counts per second) were normalized to β-galactosidase activity (mU). Asterisks indicate significant decreases (p, 0.05) in transactivation compared to uninhibited Tat-FLAG (first column). Columns represent the means and standard deviations of three independent experiments.

To investigate the molecular effects of transdominant Tat mutants, a novel mutant termed Nullbasic was created. Unlike previous studies, we mutated the full length, 101 amino-acid form of Tat since we noted that two-exon Tat is expressed at greater levels that one-exon Tat in most cell lines, and that two-exon Tat is the primary form expressed by HIV-1 clinical isolates (Jeang et al., 1999). Nullbasic was engineered from the BH10 clone of Tat (101 amino acid variant) by replacing the basic domain with a glycine/alanine sequence and fusing the FLAG epitope tag to the carboxy terminus (FIG. 1A). One-exon transdominant Tat mutants with altered or deleted basic domains have previously been shown to localize predominantly to the cytoplasm of cells (Hauber et al., 1999; Pearson et al., 1990; Orsini & Debouck, 1996). To see if Nullbasic similarly localizes to the cytoplasm, HeLa cells expressing Nullbasic or the wild type Tat-FLAG fusion protein were visualized by indirect immunofluorescence microscopy using anti-FLAG antibody. As expected, wild type Tat showed strong nuclear staining, whereas Nullbasic (like the one-exon transdominant Tat mutants) was mainly localized in the cytoplasm (FIG. 1B). The defining feature of one-exon transdominant Tat mutants is their ability to suppress transactivation by wild type Tat (Pearson et al., 1990; Orsini & Debouck, 1996; Ulich et al., 1996; Echetebu et al., 1994; Rossi et al., 1997). To determine whether Nullbasic had similar activity, HeLa cells were co-transfected with equal amounts of plasmid encoding wild type Tat-FLAG, a luciferase-based HIV LTR transactivation reporter, a constitutive β-galactosidase expression vector and increasing amounts of plasmid encoding Nullbasic. The molar ratios of Tat-FLAG to Nullbasic plasmids assayed were 1:1, 1:10 and 1:20. At the 1:10 and 1:20 ratios (FIG. 2, lanes 3 and 4, respectively), Nullbasic significantly suppressed transactivated luciferase expression compared to Tat transactivation in the absence of Nullbasic (lane 1). This effect was specific to Tat since Nullbasic did not significantly affect the CMV promoter-driven expression of β-galactosidase (data not shown). Thus Nullbasic is a transdominant inhibitor of Tat-mediated transactivation.

Expression of Nullbasic in Cells Inhibits HIV-1 Production. To determine whether Nullbasic affects virus production, Nullbasic was co-expressed with a modified HIV-1 proviral construct, pGCH, in which the 59 LTR U3 region has been replaced by the CMV immediate-early promoter. The promoter is thus a hybrid of the CMV promoter and the R and U5 regions of the HIV-1 LTR. This construct enables Tat-independent HIV-1 gene expression due to the presence of the CMV promoter, thereby allowing the investigation of any transactivation-independent effects of Nullbasic on the viral replication cycle. Virions were generated in HEK293T cells co-transfected with 1:4 molar ratios of pGCH provirus to wild type Tat-FLAG, Nullbasic or empty vector ("No Tat") plasmids. Virion samples were then assayed for capsid (CA) and reverse transcriptase (RT) protein concentrations by ELISA and colorimetric enzyme assay, respectively. The concentration of CA was 10-fold lower in supernatants from cells expressing pGCH and Nullbasic compared to cells expressing pGCH and Tat-FLAG (FIG. 3A). The concentration of RT was similarly decreased, indicating that Nullbasic expression suppressed overall virus production. To discount transdominant effects of Nullbasic on the CMV/LTR hybrid promoter of pGCH, a reporter construct expressing Rev-independent HIV-1 envelope (Env) (Smulevitch et al., 2006) from the CMV/LTR promoter was co-expressed with Nullbasic in HEK293T cells. Nullbasic had no effect on the expression of Env from this reporter (FIG. 3B), indicating that Nullbasic does not significantly affect expression from the CMV/LTR promoter. Taken together, these experiments suggest that Nullbasic substantially reduces virion production by a mechanism independent of the inhibition of Tat transactivation. To further examine the production of HIV-1 viral proteins, Western blotting was performed on β-galactosidase-equalized lysates of cells co-expressing pGCH provirus and either Nullbasic or Tat-FLAG. FIG. 3C shows that provirus-expressed Gag levels were reduced in the presence of Nullbasic (lanes 4 and 5) compared to Tat-FLAG (lanes 2 and 3). Gag-related proteolytic products, specifically HIV-1 p41 gag (MA-CA) and CA, were proportionally reduced. This is consistent with the reduction in virion CA and RT protein levels observed in the supernatants of cells co-expressing Nullbasic (FIG. 3A). Expression of HIV-1 Env in the lysates was also reduced in the presence of Nullbasic (FIG. 3C). The decrease in Env levels by Nullbasic appeared to be greater than the decrease in Gag levels, but this is likely due to differences in antibody sensitivities since subsequent Western blot analyses of purified virions showed CA and envelope surface antigen (SU) levels to be proportional when HIV-1 was co-expressed with either Nullbasic or Tat-FLAG (FIG. 3D). Finally, co-expression of Nullbasic did not significantly affect packaging of viral genomic RNA into HIV-1 virions compared to co-expression of Tat-FLAG (FIG. 3E). These experiments demonstrate that Nullbasic potently inhibits HIV-1 gene expression, leading to decreased production of the viral structural proteins without altering the relative protein or RNA compositions of virions.

Nullbasic Down-regulates Unspliced and Singly-Spliced HIV-1 mRNA Levels in Cells.

Expression of HIV-1 Gag and Env require nuclear export of unspliced and singly-spliced mRNA, respectively, by the viral Rev protein. Since transcription from pGCH is Tat independent, the observed down-regulation of Env and Gag protein levels in FIG. 3C could thus be due to Nullbasic interfering with HIV-1 mRNA nuclear export. To test this possibility, Northern blot analysis was performed to determine the relative proportions of HIV-1 mRNA species produced in the presence of Nullbasic. HIV-1 mRNAs isolated from HEK293T cells co-expressing pGCH provirus and either Tat-FLAG or Nullbasic were detected with a single, probe capable of binding to the unspliced, singly-spliced and multiply-spliced classes of HIV-1 transcripts. FIG. 4A shows that both unspliced and singly-spliced mRNA had reduced intensities in the presence of Nullbasic (lanes 4 and 5) compared to an empty vector control (lane 1) or wild type Tat-FLAG (lanes 2 and 3). In contrast, multiply-spliced transcript levels were relatively unaffected by Nullbasic (compare lanes 4 and 5 to lanes 1 to 3). To confirm these results, quantitative RT-PCR was used to measure the effect of Nullbasic on viral mRNA levels (FIG. 4B). Compared to viral mRNA levels in the absence of over-expressed Tat, Tat-FLAG caused a modest decrease in all mRNA classes. Strikingly, however, Nullbasic induced strong suppression of unspliced and singly-spliced transcripts with little effect on multiply-spliced mRNA, in close agreement with the Northern blot analysis (FIG. 4A). Nullbasic therefore reduces the steady state levels of Rev-dependent viral mRNA.

Nullbasic Alters Rev Subcellular Localization and Inhibits Proviral Rev Function.

Figure 5:
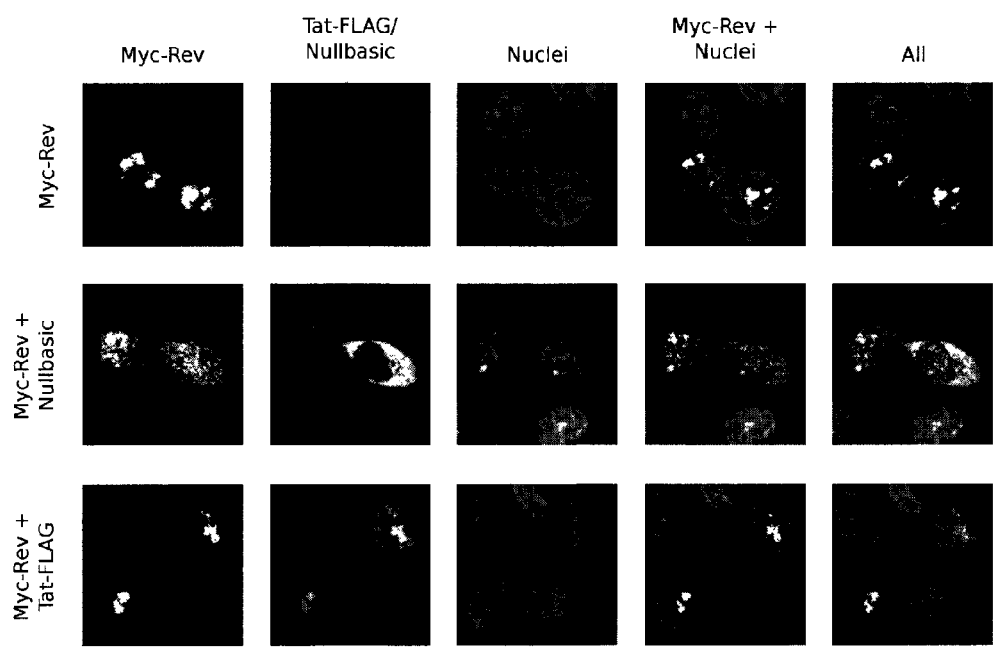
FIG. 5. Nullbasic alters the subcellular localization of HIV-1 Rev. HeLa cells expressing a Myc-Rev fusion protein alone (top row), Myc-Rev with Nullbasic (middle row) or Myc-Rev with Tat-FLAG (bottom row) were visualized by confocal microscopy using anti-Myc/Cy3 and anti-FLAG/FITC antibodies. Nuclei were stained with DAPI. The total amounts of transfected plasmids in each experiment were normalized with empty vector (pcDNA3.1+). Images are representative of at least five fields per slide from three independent experiments.
Figure 6:
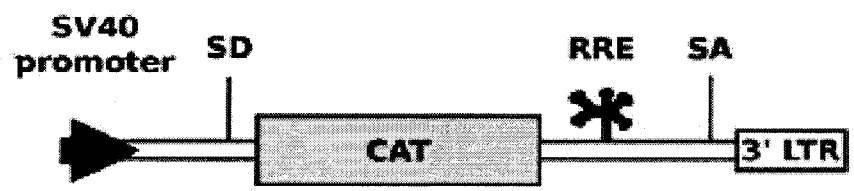
FIG. 6. Nullbasic inhibits the RNA export function of provirus-expressed Rev. (A) Schematic diagram of the Rev-dependent CAT expression cassette in plasmid pDM128. The chloramphenicol acetyltransferase (CAT) gene exists within an artificial intron bounded by splice donor (SD) and splice acceptor (SA) sequences. Successful expression of CAT protein requires binding of Rev to the Rev response element (RRE) to avoid intron splicing and to enable nuclear export of the CAT mRNA transcript. SV40: simian virus 40; 39 LTR: HIV-1 long terminal repeat (contains polyadenylation signal). (B) HEK293T cells were co-transfected with pDM128 and pGCH provirus alone (column 2), Myc-Rev plasmid alone (column 4) or along with Nullbasic plasmid (columns 3 and 5). Empty vector (pcDNA3.1+) was used to normalize the total amount of transfected plasmids. A pDM128 only transfection was included as a negative control (column 1) and a constitutive β-galactosidase plasmid was included in all transfections to account for variations in transfection efficiencies. CAT expression was measured by ELISA and is expressed relative to β-galactosidase activity (ng/mU). Columns represent means and standard deviations of three independent experiments. (C) Lysates from cells expressing a Rev-independent Gag-FLAG fusion protein co-transfected with empty vector (lane 1) or co-expressing either Tat-FLAG (lanes 2 and 3; 1:2 and 1:4 molar ratio, respectively) or Nullbasic (lanes 4 and 5; 1:2 and 1:4 molar ratio, respectively) were immunoblotted with anti-FLAG antibody to detect all three proteins. The white band centers in lanes 3 and 5 are due to luminol precipitation, indicative of very high amounts of Tat-FLAG and Nullbasic protein, respectively, on the membrane. Data are representative of three independent experiments.
Figure 6:
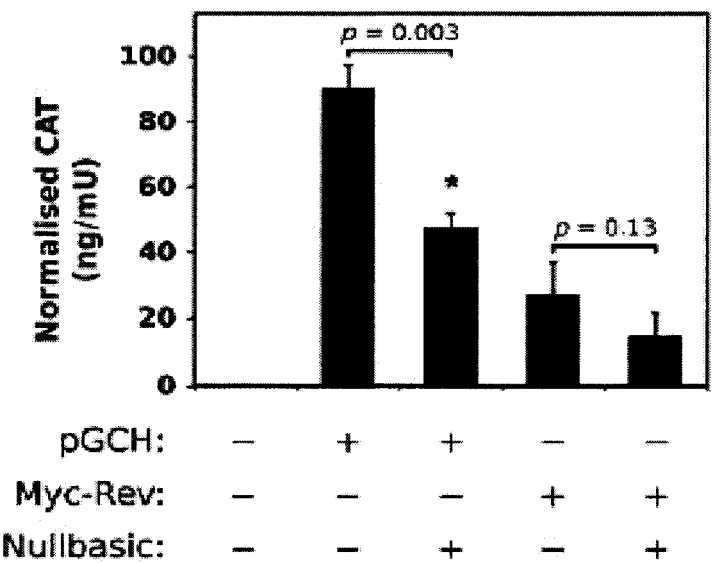
Figure 6:
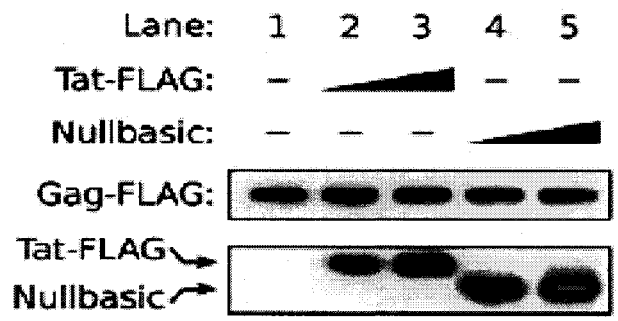

HIV-1 Rev promotes the nuclear export of unspliced and singly-spliced viral mRNA by directly binding to the Rev response element (RRE) contained within these viral mRNAs. In the absence of Rev, multiple splicing events lead to the removal of sequences encoding Gag and Env. Rev: mRNA complexes traffic from the nucleus to the cytoplasm via the CRM1 export pathway (Felber et al., 2007). Rev traffics between the nucleus, nucleolus and cytoplasm to execute its mRNA export function, and previous reports implied that Tat and Rev share common trafficking mechanisms (Li, 1997; Truant & Cullen, 1999). Nullbasic could therefore interfere with Rev localization. To test this hypothesis, indirect immunofluorescence was performed on HeLa cells co-expressing Myc-Rev (a fusion between the MYC epitope tag and HIV-1 Rev) and either Nullbasic or Tat-FLAG using anti-MYC/Cy3 and anti-FLAG/FITC antibodies. Myc-Rev expressed alone accumulated in nuclear structures consistent with nucleoli, as observed previously (Dundr et al., 1995) (FIG. 5). Co-expression with Nullbasic, however, caused substantial redistribution of Myc-Rev to the nucleoplasm and cytoplasm (FIG. 5, row 2). In contrast, co-expression with Tat-FLAG did not change Myc-Rev nucleolar localization (FIG. 5, row 3). These patterns of Myc-Rev distribution were frequently observed throughout the entire slide and were confirmed in two independent experiments. The results therefore illustrate that Nullbasic can alter the subcellular localization of Rev. However, immunoprecipitation analyses showed no substantial interaction between Myc-Rev and Nullbasic (data not shown). Together these data indicate that Nullbasic can alter Rev subcellular localization by an undetermined mechanism. To assess whether Nullbasic could down-regulate the mRNA export function of Rev, a Rev reporter assay was used that makes use of the pDM128 plasmid (FIG. 6A) (Hope et al., 1990). In the absence of Rev, the host-cell splicing machinery removes the chloramphenicol acetyltransferase (CAT) open reading frame from mRNA transcripts expressed by the plasmid's SV40 promoter (FIG. 6A), resulting in no production of CAT protein. In the presence of Rev, the splicing machinery is bypassed when Rev interacts with the RRE element present in pDM128 transcripts, thereby allowing CAT protein expression. When the pGCH provirus was used to provide Rev in the reporter assay, co-expression of Nullbasic resulted in a statistically-significant decrease (p=0.003) of CAT protein levels compared with no Nullbasic co-expression (FIG. 6B). When we used the Myc-Rev expression plasmid to provide Rev in the assay, Nullbasic appeared to inhibit CAT protein levels but this was determined not to be significant (FIG. 6B; p=0.13, compared to no Nullbasic co-expression). Nullbasic alone did not induce CAT expression and down-regulation of Rev function was not caused by diminished proviral Rev steady state (data not shown). The results therefore suggest that Nullbasic can inhibit proviral Rev-mediated mRNA export, possibly requiring the presence of other viral factors to induce this inhibition. To provide further evidence that Nullbasic inhibits Rev-mediated mRNA export function, a Gag-FLAG fusion protein expressed from a plasmid in which inhibitory sequences had been silenced to allow Rev-independent Gag production (Tritel & Resh, 2000) was co-expressed with Nullbasic. In contrast to wild type Gag (FIG. 3C), the steady state levels of Rev-independent Gag-FLAG were the same in the presence of both Tat-FLAG and Nullbasic (FIG. 6C), indicating that Nullbasic had no effect on Gag expression or protein levels when the requirement for Rev was bypassed. Together the data therefore suggest that Nullbasic interferes with the mRNA export function of HIV-1 Rev.

Nullbasic Inhibits HIV-1 Infectivity and Reverse Transcription.

Figure 7:
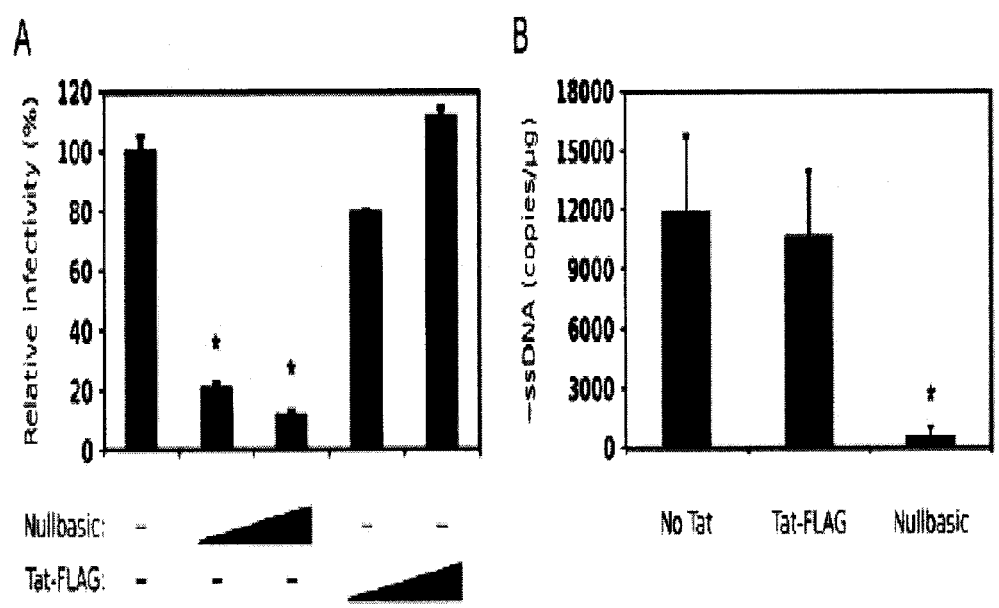
FIG. 7. Nullbasic inhibits HIV-1 infectivity and endogenous reverse transcription. (A) The infectivity of HIV-1 produced by HEK293T cells expressing pGCH provirus co-transfected with empty vector (pcDNA3.1+) or co-expressing increasing amounts of Nullbasic or Tat-FLAG (at 1:2 and 1:4 molar ratios) were determined by the MAGI assay. The indicator cells were infected with virion samples equalized for reverse transcriptase activity before cell lysates were assayed for β-galactosidase production 48 h later. Columns represent the means and standard deviations of three independent experiments and are expressed as a percentage of the "No Tat" sample (column 1). Asterisks indicate significant differences (p, 0.05) in infectivities compared to the "No Tat" sample. (B) Detergent-free endogenous reverse transcription assays were performed with the same virus samples as in A. The amount of negative-strand strong-stop DNA (−ssDNA) was quantitated by PCR, and normalized to the RT activity in each sample. The asterisk indicates a significant difference (p, 0.05) in −ssDNA synthesis relative to the "No Tat" sample, and columns represent the means and standard deviations of duplicate assays in three independent experiments.

We next compared the infectivity of virions produced in the presence and absence of Nullbasic. Infectivity was tested using HeLa-CD4-LTR-β-gal reporter (MAGI) cells, which contain a stably-integrated LTR-β-galactosidase expression cassette that reports productive HIV-1 infection following Tat expression and transactivation (Kimpton & Emerman, 1992) Virion samples tested in the assay were always normalized for RT activity. We observed that HIV-1 virions produced by Nullbasic-expressing cells had significantly reduced infectivities compared to virons produced by Tat-FLAG-expressing cells (FIG. 7A). This was evident when the molar ratio of pGCH to Nullbasic plasmid was 1:2 and 1:4. Nullbasic therefore reduces HIV-1 infectivity when expressed in the virus producer cells. A detergent-free endogenous reverse transcription assay was used to determine whether virions produced by Nullbasic-expressing cells were able to initiate reverse transcription (Apolloni et al., 2007). There was an 18-fold decrease in minus-strand strong-stop DNA (–ss-DNA) synthesis, an early product of reverse transcription, in virions produced in the presence of Nullbasic compared to virions produced in the presence of Tat-FLAG (FIG. 7B). These data suggest that the suppression of virion infectivity was primarily due to a Nullbasic-induced defect in reverse transcription.

HIV-1 Replication Is Potently Inhibited in a Permissive Cell Line Stably Expressing Nullbasic.

We next investigated if expression of Nullbasic in permissive target cells can confer resistance to HIV-1 infection. To enable convenient monitoring of Nullbasic expression, the enhanced green fluorescent protein (EGFP) was fused to the carboxy terminal of Nullbasic. Fusion of EGFP to Nullbasic did not alter its antiviral activity compared to unfused Nullbasic (FIG. 8A). Nullbasic-EGFP was stably introduced into MAGI cells via lentivirus-mediated transduction (Salmon et al., 2000), and highly expressing cells were isolated by fluorescence-activated cell sorting (FACS). A control cell line expressing only EGFP (MAGI/EGFP) was similarly derived. Stable expression of Nullbasic-EGFP and EGFP was retained in the respective cell lines after several passages, as demonstrated by both fluorescence microscopy and Western blotting (data not shown). Lentiviral transduction was determined by flow cytometry not to alter either transgenic CD4 (FIG. 8B) or endogenous CXCR4 (FIG. 8C) receptor levels in the MAGI/Nullbasic-EGFP cell line. The parental and transduced cell lines were challenged with equal amounts of HIV-1 virions (500 ng CA-equivalent per 106 cells) and cultured for 14 days. Virus production from the cells was monitored over time by CA ELISA of the culture supernatants. A rapid increase in virus production in both the parental MAGI and MAGI/EGFP cell lines was seen over the first 9 days before syncytia formation and cell death were observed (FIG. 8D). In contrast, a greater than two-log reduction in virus production was observed in the MAGI/Nullbasic-EGFP cell line, with no syncytia formation or cell death being apparent even at the end of the experiment. These results were confirmed in two independently derived MAGI/Nullbasic-EGFP cell lines. Expression of Nullbasic in permissive cells is therefore protective against HIV-1 challenge and suppresses viral spread.

EXAMPLE 2

Materials & Methods

MLV Retroviral Vector and VLP Production.

Nullbasic was inserted into the Murine leukaemia virus (MLV)-based retroviral vector pSAMEN. This was transfected into Phoenix cells, a human HEK293T cells line, which was subsequently used to make virus like particles.

Human T Cells Expressing Nullbasic.

A human T-cell line called Jurkat was transduced with a Murine VLP capable of delivering Nullbasic fused to the EGFP protein, or with the same vector delivering EGFP alone. Cells expressing Nullbasic-EGFP or EGFP were identified by flow cytometry and collected by FACS. The cells were expanded by culturing in growth media and Nullbasic-EGFP and EGFP expression in the cells was confirmed by Western blot analysis.

Infection of Jurkat Cells with HIV-1.

Stably transduced Jurkat cells were infected with HIV-1. In addition, the original non-transduced Jurkat cell line was infected as an additional control. For each infection, 1 e⁶ cells where infected with HIV-1 equivalent to 25 or 100 ng of capsid protein (CAp24) for 2 hours. Each infection was performed in triplicate (six experiments in total). The residual HIV-1 was removed by two successive washing in culture media and samples from each culture was sampled on Days 0, 1, 4, 7, and 11. HIV-1 replication was monitored by measuring HIV-1 CAp24 by ELISA.

Results

There was a sharp reduction in HIV-1 CAp24 production in Jurkat cells expressing Nullbasic-EGFP compared to control cells expressing EGFP or in the parental Jurkat cells. This indicates that Nullbasic inhibited HIV-1 replication.

Discussion

Figure 3:
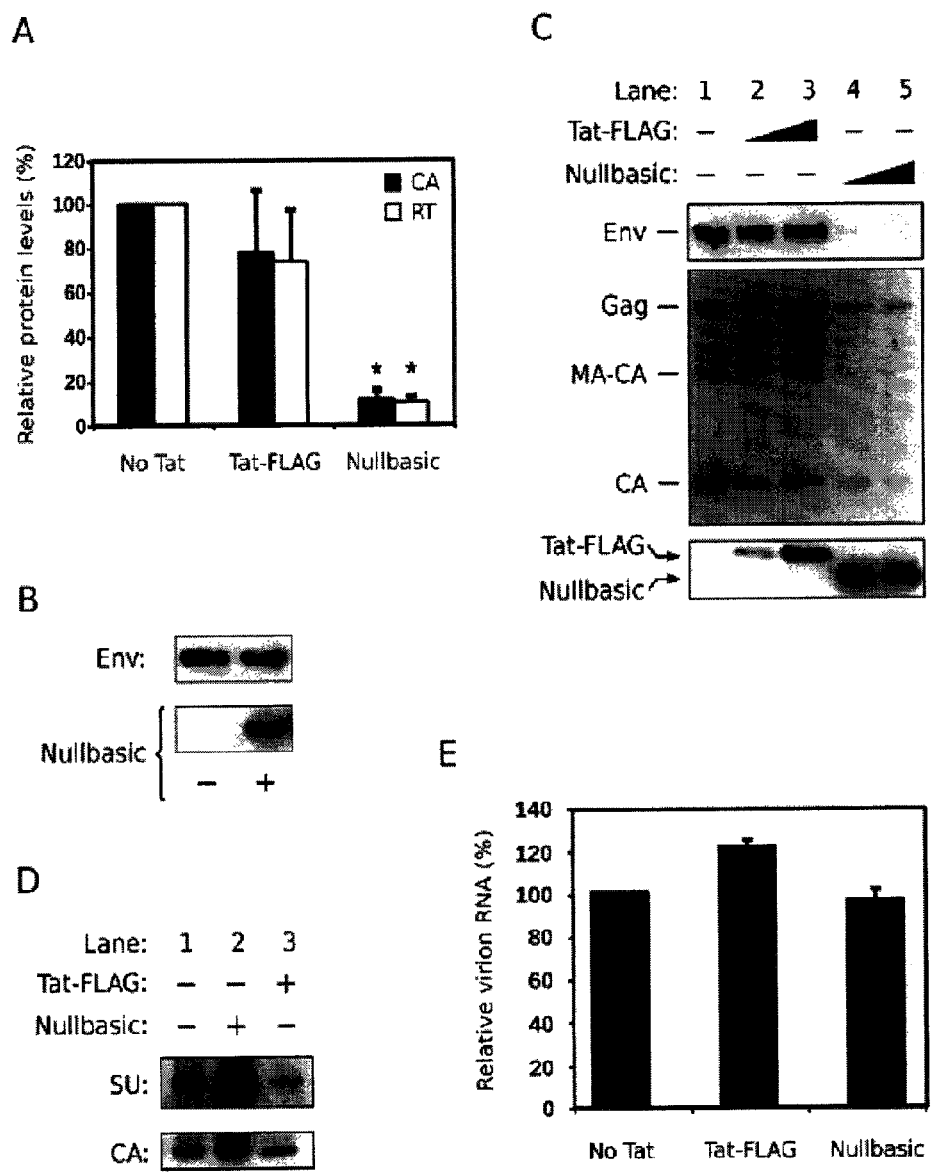
FIG. 3. Nullbasic inhibits HIV-1 virion production but not composition. (A) Virions produced in HEK293T cells co-transfected with 1:4 molar ratios of HIV-1 plasmid (pGCH) to Tat-FLAG, Nullbasic or empty vector (pcDNA3.1+; "No Tat") plasmids were assayed for capsid (CA) and reverse transcriptase (RT) concentrations. The CA (black columns) and RT (white columns) concentrations are shown. Columns represent the means and standard deviations of four independent experiments and are expressed as a percentage of the "No Tat" sample. Asterisks indicate significant differences (p, 0.025, Welch's t-test) in CA and RT concentrations between Nullbasic and Tat-FLAG samples. (B) HEK293T cells transfected with a reporter plasmid that expresses Rev-independent Env from the CMV/LTR hybrid promoter of pGCH were co-expressed with (lane 2) or without (lane 1) Nullbasic. Env and Nullbasic were detected by immunoblotting with anti-gp120 and anti-FLAG antibodies, respectively. (C) Cell lysates from HEK293T cells expressing pGCH provirus alone (lane 1) or co-expressing either Tat-FLAG (lanes 2 and 3; 1:2 and 1:4 molar ratios, respectively) or Nullbasic (lanes 4 and 5; 1:2 and 1:4 molar ratios, respectively) were immunoblotted with a monoclonal antibody against HIV-1 SU (upper panel), anti-serum against HIV (middle panel) and a monoclonal antibody against FLAG (lower panel). A β-galactosidase expression plasmid was included in all transfections and Western blotting was performed on lysates normalised for β-galactosidase activity. (D) Culture supernatants were collected from HEK293T cells expressing pGCH alone (lane 1) or co-expressing either Nullbasic (lane 2) or Tat-FLAG (lane 3). Virions in the supernatants were concentrated by ultracentrifugation before samples containing 50 ng of total CA were immunoblotted with anti-gp120 and anti-CA antibodies. Data in B, C and D are representative of three independent experiments. (E) Packaged genomic RNA was isolated from virions produced by HEK293T cells expressing pGCH co-transfected with empty vector (pcDNA3.1+; "No Tat") or co-expressing Tat-FLAG or Nullbasic before being quantitated by RT-PCR. The means and standard deviations of two experiments performed in duplicate on independent virus stocks are shown, with values expressed as a percentage of the "No Tat" sample.
Figure 4:
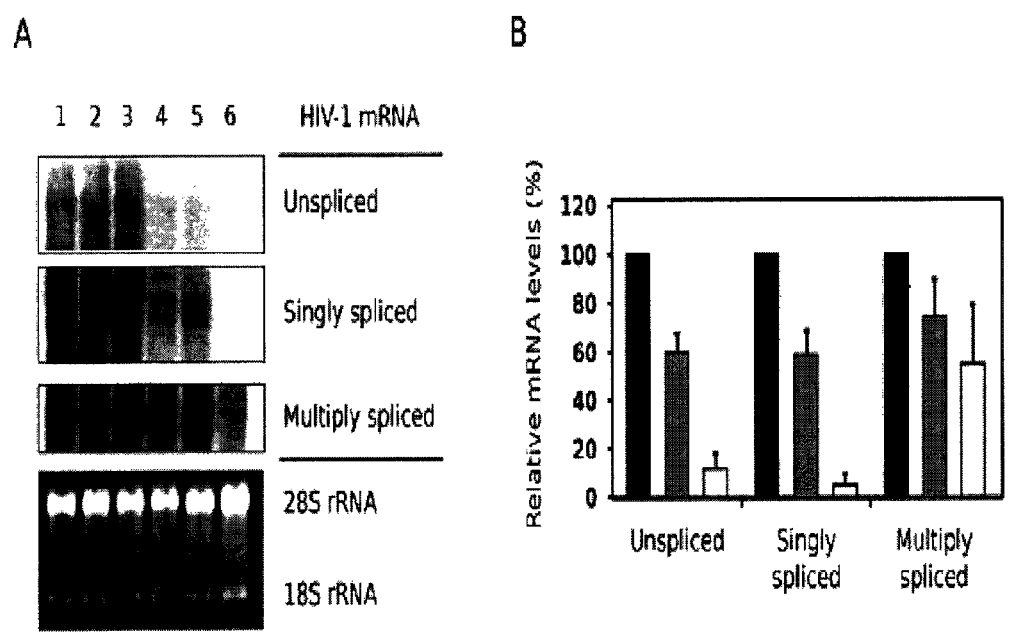
FIG. 4. Nullbasic down-regulates the levels of unspliced and singly-spliced HIV-1 mRNA expressed in cells. (A) Northern blot analysis of total RNA from HEK293T cells expressing pGCH provirus co-transfected with empty vector (pcDNA3.1+; "No Tat", lane 1) or co-expressing increasing amounts of Tat-FLAG (lanes 2 and 3; 1:2 and 1:4 molar ratios, respectively) or Nullbasic (lanes 4 and 5; 1:2 and 1:4 molar ratios, respectively). An untransfected control was also included (lane 6). Unspliced, singly-spliced and multiply-spliced HIV-1 mRNA were detected with a single HIV-1-specific probe. 28S and 18S ribosomal RNA (rRNA) species demonstrate equal sample loading. Data are representative of four independent experiments. (B) Total RNA was extracted from HEK293T cells expressing pGCH co-transfected with empty vector (black bars) or co-expressing Tat-FLAG (gray bars) or Nullbasic (white bars) before RT-PCR reactions were performed using primers specific to unspliced, singly-spliced and multiply-spliced viral mRNA. Tat-FLAG and Nullbasic plasmids were transfected at 2:1 molar ratios with respect to pGCH. The means and standard deviations of duplicate assays in three independent experiments are shown, with values for each mRNA class expressed as a percentage of the pGCH alone sample.
Figure 8:
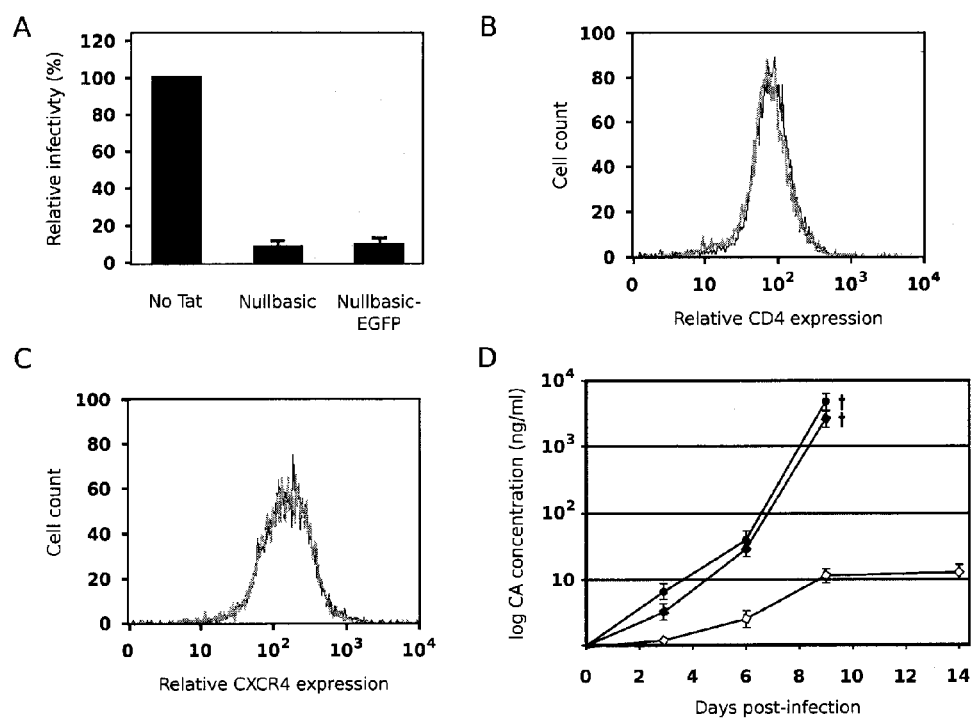
FIG. 8. Expression of Nullbasic-EGFP in permissive target cells suppresses HIV-1 infection and spread. (A) The ability of Nullbasic-EGFP to inhibit HIV-1 infectivity was compared to Nullbasic in a MAGI assay similar to FIG. 7A (using a 1:2 molar ratio only). Columns represent the means and standard deviations of three independent experiments and are expressed as a percentage of the "No Tat" (pcDNA3.1+ co-transfected) sample. (B) Cell surface expression of transgenic CD4 receptors was quantitated in MAGI (black) and MAGI/Nullbasic-EGFP (gray) cells by flow cytometry using an anti-CD4 monoclonal antibody. (C) Cell surface expression of endogenous CXCR4 receptors was quantitated in MAGI (black) and MAGI/Nullbasic-EGFP (gray) cells by flow cytometry using an anti-CXCR4 monoclonal antibody. (D)

Transdominant-negative Tat mutants have to date been defined by their abilities to suppress the transactivation function of HIV-1 Tat (Pearson et al., 1990; Orsini & Debouck, 1996; Ulich et al., 1996; Echetebu et al., 1994; Rossi et al., 1997). Here we describe for the first time a full-length, transdominant two-exon Tat mutant, termed Nullbasic (FIG. 1A), and demonstrate its potent inhibitory activity against multiple stages of the HIV-1 replication cycle. In addition to suppressing Tat transactivation (FIG. 2), Nullbasic reduced HIV-1 virion production by suppressing Rev-dependant RNA export (FIGS. 3 and 4) and virus produced in the presence of Nullbasic was severely defective for reverse transcription (FIG. 7B). As a result of these multiple inhibitory activities, expression of Nullbasic in permissive cells conferred strong resistance against high-dose HIV-1 challenge and the reduction by greater than two orders of magnitude of a spreading viral infection (FIG. 8). This is the first demonstration of a transdominant Tat mutant that targets multiple, distinct steps in the HIV-1 replication cycle: proviral gene transcription, Rev-dependent mRNA transport and reverse transcription. Nullbasic down-regulated the expression of Gag and Env from a HIV-1 proviral plasmid that expressed viral mRNA from a CMV promoter (FIG. 3C). Two different assays, quantitation of viral mRNA (FIG. 4) and a functional assay (FIG. 6), pointed to a defect in Rev mRNA export function. Nullbasic disrupted Rev distribution (FIG. 5) and function leading to decreased steady state levels of unspliced and singly-spliced viral mRNA, resulting in the observed down-regulation of Gag and Env protein levels, respectively. Interestingly, Nullbasic did not significantly affect the mRNA export function of ectopically-expressed Rev (FIG. 6B, Myc-Rev), suggesting that a complex interaction between Nullbasic, Rev and other HIV-1 factors is required to inhibit viral mRNA export. Furthermore, the data imply that Nullbasic inhibits Rev function via an indirect mechanism. Further investigation is required to determine which viral or cellular factor intermediates between Nullbasic and Rev to enable viral mRNA export inhibition. Rev normally binds the Rev response element (RRE), an RNA structure located within HIV-1 env, to facilitate export of unspliced and singly-spliced mRNA from the nucleus. A dominant-negative Rev mutant called M10 has been described that was shown to inhibit wild type Rev function (Malim et al., 1991). The M10 mutant protein is dominant negative because it retains the ability to bind the HIV-1 RRE but is unable to promote export of the viral mRNA from the nucleus, thereby inhibiting HIV-1 replication (Malim et al., 1991; Stauber et al., 1995). Our data suggest that Nullbasic and M10 inhibit Rev by different mechanisms. Confocal microscopy experiments indicated that Nullbasic can disrupt Rev subcellular localization (FIG. 5). The nucleolar localization of Rev appears to be important for its function (Dundr et al., 1995; Cochrane et al., 1990), so the Nullbasic-induced redistribution of Rev from nucleolus to nucleoplasm and cytoplasm is likely to be necessary, but is not sufficient, to inhibit Rev function. There are reports that Tat and Rev share common nuclear trafficking pathways involving importin b (Truant & Cullen, 1999) and B23 (nucleophosmin) (Li, 1997; Dundr et al., 1995), so it is possible that Nullbasic may directly interfere with Rev trafficking. Tat trafficking, however, remains controversial, with conflicting reports that Tat nuclear accumulation requires active, factor-dependent pathways (Efthymiadis et al., 1998) or passive, factor-independent mechanisms (Cardarelli et al., 2007). The lack of a demonstrable interaction between Nullbasic and Myc-Rev in immunoprecipitation experiments (unpublished observations) suggests that Nullbasic interferes with Rev trafficking by an indirect mechanism. Conceivably, Nullbasic may sequester cellular factors (such as importins) normally required for Rev nucleolar targeting. Whatever the mechanism, disruption of Rev trafficking and therefore HIV-1 mRNA export function represents a major antiviral activity of Nullbasic. The third major activity of Nullbasic was abrogation of intravirion reverse transcription activity (FIG. 7B). Co-expression of Nullbasic in virus producer cells did not alter the RNA content of virions (FIG. 3E), indicating that Nullbasic does not affect HIV-1 genomic RNA packaging. Tat is usually only present in virions at very low concentrations (Chertova et al., 2006). However, increased nonspecific inclusion of Nullbasic into virions may occur due to the high cytoplasmic concentrations of Nullbasic (FIG. 1B). Once in the virion, Nullbasic may have a dominant negative effect on Tat-mediated enhancement of reverse transcription (Apolloni et al., 2007). Alternatively, Nullbasic may negatively affect nucleocapsid activity, which was recently reported to precisely regulate reverse transcription (Houzet et al., 2008). Nullbasic might also bind other crucial intravirion factors and thereby indirectly disrupt the regulation of reverse transcription. Whatever the mechanism, virions produced by cells expressing Nullbasic have low infectivity due to a reverse transcription defect. The therapeutic value of Nullbasic is illustrated by experiments showing that Nullbasic expression protected cells from high-dose HIV-1 infection (FIGS. 8D, 9, 10, and 11), particularly when a Murine leukaemia virus (MLV)-based retroviral vector was used (see FIGS. 9-11). Furthermore, Nullbasic-expressing cells were protected against HIV-1-induced syncytia formation and cell death, indicating that Nullbasic expression protected cells against a spreading infection. All three of the previously described antiviral activities of Nullbasic (inhibition of transactivation, Rev function and reverse transcription) likely combined to suppress this spreading infection. In conclusion, we demonstrate the potent antiviral activity of a transdominant Tat mutant and show that multiple steps in the HIV-1 replication cycle are targeted. In addition to negative effects on viral gene expression, we report for the first time that Nullbasic also inhibits Rev-dependent viral mRNA transport and intravirion reverse transcription. Moreover, these inhibitory effects combined potently to reduce HIV infection, illustrating Nullbasic and its activities as potential avenues for the development of new therapeutic interventions. Identification of the cellular or viral factors that interact with Nullbasic to induce Rev and reverse transcription inhibition may also reveal novel aspects of HIV-1 replication.

REFERENCES

Apolloni A, Hooker C W, Mak J, Harrich D (2003) Human immunodeficiency virus type 1 protease regulation of tat activity is essential for efficient reverse transcription and replication. *J Virol* 77: 9912-9921.

Apolloni A, Meredith L W, Suhrbier A, Kiernan R, Harrich D (2007) The HIV-1 Tat protein stimulates reverse transcription in vitro. *Curr HIV Res* 5: 473-483.

Arrigo S J, Weitsman S, Zack J A, Chen I S (1990) Characterization and expression of novel singly spliced RNA species of human immunodeficiency virus type 1. *J Virol* 64: 4585-4588.

Barillari G, Gendelman R, Gallo R C, Ensoli B (1993) The Tat protein of human immunodeficiency virus type 1, a growth factor for AIDS Kaposi sarcoma and cytokine-activated vascular cells, induces adhesion of the same cell types by using integrin receptors recognizing the RGD amino acid sequence. *Proc Natl Acad Sci USA* 90: 7941-7945.

Berkhout B, Silverman R H, Jeang K T (1989) Tat trans-activates the human immunodeficiency virus through a nascent RNA target. *Cell* 59: 273-282.

Bradford M M (1976) A rapid and sensitive method for the quantitation of microgram quantities of protein utilizing the principle of protein-dye binding. *Anal Biochem* 72: 248-254.

Cardarelli F, Serresi M, Bizzarri R, Giacca M, Beltram F (2007) In vivo study of HIV-1 Tat arginine-rich motif unveils its transport properties. *Mol Ther* 15: 1313-1322.

Chertova E, Chertov O, Coren L V, Roser J D, Trubey C M, et al. (2006) Proteomic and biochemical analysis of purified human immunodeficiency virus type 1 produced from infected monocyte-derived macrophages. *J Virol* 80: 9039-9052.

Cochrane A W, Perkins A, Rosen C A (1990) Identification of sequences important in the nucleolar localization of human immunodeficiency virus Rev: relevance of nucleolar localization to function. *J Virol* 64: 881-885.

Dayton A I, Sodroski J G, Rosen C A, Goh W C, Haseltine W A (1986) The transactivator gene of the human T cell lymphotropic virus type III is required for replication. *Cell* 44: 941-947.

Dundr M, Leno G H, Hammarskjold M L, Rekosh D, Helga-Maria C, et al. (1995) The roles of nucleolar structure and function in the subcellular location of the HIV-1 Rev protein. *J Cell Sci* 108: 2811-2823.

Echetebu C O, Rhim H, Herrmann C H, Rice A P (1994) Construction and characterization of a potent HIV-2 Tat transdominant mutant protein. *J Acquir Immune Defic Syndr* 7: 655-664.

Efthymiadis A, Briggs L J, Jans D A (1998) The HIV-1 Tat nuclear localization sequence confers novel nuclear import properties. *J Biol Chem* 273: 1623-1628.

Eustice D C, Feldman P A, Colberg-Poley A M, Buckery R M, Neubauer R H (1991) A sensitive method for the detection of beta-galactosidase in transfected mammalian cells. *Biotechniques* 11: 739-740, 742-733.

Felber B K, Zolotukhin A S, Pavlakis G N (2007) Posttranscriptional control of HIV-1 and other retroviruses and its practical applications. *Adv Pharmacol* 55: 161-197.

Hauber J, Malim M H, Cullen B R (1989) Mutational analysis of the conserved basic domain of human immunodeficiency virus tat protein. *J Virol* 63: 1181-1187.

Hauber J, Perkins A, Heimer E P, Cullen B R (1987) Transactivation of human immunodeficiency virus gene expression is mediated by nuclear events. *Proc Natl Acad Sci USA* 84: 6364-6368.

Hope T J, McDonald D, Huang X J, Low J, Parslow T G (1990) Mutational analysis of the human immunodeficiency virus type 1 Rev transactivator: essential residues near the amino terminus. *J Virol* 64: 5360-5366.

Houzet L, Morichaud Z, Didierlaurent L, Muriaux D, Darlix J L, et al. (2008) Nucleocapsid mutations turn HIV-1 into a DNA-containing virus. *Nucleic Acids Res* 36: 2311-2319.

Jeang K T, Xiao H, Rich E A (1999) Multifaceted activities of the HIV-1 transactivator of transcription, Tat. *J Biol Chem* 274: 28837-28840

Kimpton J, Emerman M (1992) Detection of replication-competent and pseudotyped human immunodeficiency virus with a sensitive cell line on the basis of activation of an integrated beta-galactosidase gene. *J Virol* 66: 2232-2239.

King J, Laemmli U K (1971) Polypeptides of the tail fibres of bacteriophage T4. *J Mol Biol* 62: 465-477.

Li Y P (1997) Protein B23 is an important human factor for the nucleolar localization of the human immunodeficiency virus protein Tat. *J Virol* 71: 4098-4102.

MacGregor G R, Caskey C T (1989) Construction of plasmids that express E. coli beta-galactosidase in mammalian cells. *Nucleic Acids Res* 17: 2365.

Malim M H, McCarn D F, Tiley L S, Cullen B R (1991) Mutational definition of the human immunodeficiency virus type 1 Rev activation domain. *J Virol* 65: 4248-4254.

Orsini M J, Debouck C M (1996) Inhibition of human immunodeficiency virus type 1 and type 2 Tat function by transdominant Tat protein localized to both the nucleus and cytoplasm. *J Virol* 70: 8055-8063.

Pearson L, Garcia J, Wu F, Modesti N, Nelson J, et al (1990) A transdominant tat mutant that inhibits tat-induced gene expression from the human immunodeficiency virus long terminal repeat. *Proc Natl Acad Sci USA* 87: 5079-5083.

Rossi C, Balboni P G, Betti M, Marconi P C, Bozzini R, et al. (1997) Inhibition of HIV-1 replication by a Tat transdominant negative mutant in human peripheral blood lymphocytes from healthy donors and HIV-1-infected patients. *Gene Ther* 4: 1261-1269.

Ruben S, Perkins A, Purcell R, Joung K, Sia R, et al. (1989) Structural and functional characterization of human immunodeficiency virus tat protein. *J Virol* 63: 1-8.

Salmon P, Oberholzer J, Occhiodoro T, Morel P, Lou J, et al. (2000) Reversible immortalization of human primary cells by lentivector-mediated transfer of specific genes. *Mol Ther* 2: 404-414.

Smulevitch S, Bear J, Alicea C, Rosati M, Jalah R, et al. (2006) RTE and CTE mRNA export elements synergistically increase expression of unstable, Revdependent HIV and SW mRNAs. *Retrovirology* 3: 6.

Stauber R, Gaitanaris G A, Pavlakis G N (1995) Analysis of trafficking of Rev and transdominant Rev proteins in living cells using green fluorescent protein fusions: transdominant Rev blocks the export of Rev from the nucleus to the cytoplasm. *Virology* 213: 439-449.

Tritel M, Resh M D (2000) Kinetic analysis of human immunodeficiency virus type 1 assembly reveals the presence of sequential intermediates. *J Virol* 74: 5845-5855.

Truant R, Cullen B R (1999) The arginine-rich domains present in human immunodeficiency virus type 1 Tat and Rev function as direct importin betadependent nuclear localization signals. *Mol Cell Biol* 19: 1210-1217.

Ulich C, Harrich D, Estes P, Gaynor R B (1996) Inhibition of human immunodeficiency virus type 1 replication is enhanced by a combination of transdominant Tat and Rev proteins. *J Virol* 70: 4871-4876.

Vivès E, Brodin P, Lebleu B (1997) A truncated HIV-1 Tat protein basic domain rapidly translocates through the plasma membrane and accumulates in the cell nucleus. *J Biol Chem* 272: 16010-16017.

Warrilow D, Meredith L, Davis A, Burrell C, Li P, et al. (2008) Cell factors stimulate human immunodeficiency virus type 1 reverse transcription in vitro. *J Virol* 82: 1425-1437.

Zufferey R, Nagy D, Mandel R J, Naldini L, Trono D (1997) Multiply attenuated lentiviral vector achieves efficient gene delivery in vivo. *Nat Biotechnol* 15: 871-875.

The invention claimed is:

1. An isolated mutant Tat protein comprising (i) an amino acid sequence of (a) an activation domain, and (b) an amino acid sequence of a modified basic domain as set forth in residues 49-57 of SEQ ID NO:1; and (ii) another amino acid sequence that is encoded by a nucleotide sequence of exon 2 of a Tat gene.

2. The isolated mutant Tat protein of claim 1, wherein (ii) comprises a glycine at a position corresponding to residue 79 of the amino acid sequence encoded by exon 2 of the Tat gene.

3. The isolated mutant Tat protein of claim 2, wherein (ii) comprises an RGD amino acid sequence, wherein the glycine is at a position corresponding to residue 79 of the amino acid sequence encoded by exon 2 of the Tat gene.

4. The isolated mutant Tat protein of claim 1, wherein said isolated mutant Tat protein is capable of modulating one or more steps of the HIV-1 replication cycle.

5. The isolated mutant Tat protein of claim 1, wherein said isolated mutant Tat protein at least partly inhibits, suppresses, prevents, or otherwise hinders, one or more biological activities selected from the group consisting of Tat transactivation, Rev-dependent viral mRNA transport, and reverse transcription.

6. A pharmaceutical composition comprising the isolated mutant Tat protein of claim 1, and a carrier, diluent or excipient.

\* \* \* \* \*

SEQUENCE LISTING

```
<160> NUMBER OF SEQ ID NOS: 9

<210> SEQ ID NO 1
<211> LENGTH: 111
<212> TYPE: PRT
<213> ORGANISM: Human immunodeficiency virus

<400> SEQUENCE: 1

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Gly Gly Gly Gly Gly Ala Gly Gly Gly Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu Ser Lys Lys Lys Val Glu Arg Glu Thr Glu
                85                  90                  95

Thr Asp Pro Phe Asp Gly Gly Asp Tyr Lys Asp Asp Asp Asp Lys
            100                 105                 110

<210> SEQ ID NO 2
<211> LENGTH: 101
<212> TYPE: PRT
<213> ORGANISM: Human immunodeficiency virus

<400> SEQUENCE: 2

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu Ser Lys Lys Lys Val Glu Arg Glu Thr Glu
                85                  90                  95

Thr Asp Pro Phe Asp
            100

<210> SEQ ID NO 3
<211> LENGTH: 9
<212> TYPE: PRT
<213> ORGANISM: Human immunodeficiency virus

<400> SEQUENCE: 3

Gly Gly Gly Gly Gly Ala Gly Gly Gly
1               5
```

```
<210> SEQ ID NO 4
<211> LENGTH: 26
<212> TYPE: DNA
<213> ORGANISM: Artificial Sequence
<220> FEATURE:
<223> OTHER INFORMATION: Synthetic primer

<400> SEQUENCE: 4
tctctagcag tggcgcccga acaggg                                          26

<210> SEQ ID NO 5
<211> LENGTH: 21
<212> TYPE: DNA
<213> ORGANISM: Artificial Sequence
<220> FEATURE:
<223> OTHER INFORMATION: Synthetic primer

<400> SEQUENCE: 5
gtcgccgccc ctcgcctctt g                                               21

<210> SEQ ID NO 6
<211> LENGTH: 19
<212> TYPE: DNA
<213> ORGANISM: Artificial Sequence
<220> FEATURE:
<223> OTHER INFORMATION: Synthetic primer

<400> SEQUENCE: 6
ggctcgcgat aatgtcggg                                                  19

<210> SEQ ID NO 7
<211> LENGTH: 16
<212> TYPE: DNA
<213> ORGANISM: Artificial Sequence
<220> FEATURE:
<223> OTHER INFORMATION: Synthetic primer

<400> SEQUENCE: 7
gatggtcgga agaggc                                                     16

<210> SEQ ID NO 8
<211> LENGTH: 21
<212> TYPE: DNA
<213> ORGANISM: Artificial Sequence
<220> FEATURE:
<223> OTHER INFORMATION: Synthetic primer

<400> SEQUENCE: 8
gggtctctct ggttgaccag a                                               21

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
acacaacaga cgggcacaca c                                               21
```